United States Patent
Pastore et al.

(10) Patent No.: US 8,538,520 B2
(45) Date of Patent: Sep. 17, 2013

(54) METHOD AND APPARATUS FOR DEVICE CONTROLLED GENE EXPRESSION FOR CARDIAC PROTECTION

(75) Inventors: Joseph M. Pastore, Concord, OH (US); Jeffrey Ross, Roseville, MN (US); Tamara Colette Baynham, Piscataway, NJ (US); Rodney W. Salo, Fridley, MN (US); Andrew P. Kramer, Marine on St. Croix, MN (US); Julio C. Spinelli, Buenos Aires (AR)

(73) Assignee: Cardiac Pacemakers, Inc., St. Paul, MN (US)

( * ) Notice: Subject to any disclaimer, the term of this patent is extended or adjusted under 35 U.S.C. 154(b) by 92 days.

(21) Appl. No.: 12/830,534

(22) Filed: Jul. 6, 2010

(65) Prior Publication Data

US 2010/0274306 A1    Oct. 28, 2010

Related U.S. Application Data

(62) Division of application No. 11/220,397, filed on Sep. 6, 2005, now Pat. No. 7,774,057.

(51) Int. Cl.
*A61N 1/36*    (2006.01)
(52) U.S. Cl.
USPC .......................................................... 607/9
(58) Field of Classification Search
USPC .......................................................... 607/2
See application file for complete search history.

(56) References Cited

U.S. PATENT DOCUMENTS

| | | | |
|---|---|---|---|
| 3,703,900 A | 11/1972 | Holznagel | |
| 3,716,059 A | 2/1973 | Welborn et al. | |
| 3,799,147 A | 3/1974 | Adolph et al. | |
| 3,910,260 A | 10/1975 | Sarnoff et al. | |
| 4,004,577 A | 1/1977 | Sarnoff | |
| 4,432,374 A | 2/1984 | Osanai | |
| 4,562,846 A | 1/1986 | Cox et al. | |
| 4,679,144 A | 7/1987 | Cox et al. | |
| 4,798,211 A | 1/1989 | Goor et al. | |
| 4,821,735 A | 4/1989 | Goor et al. | |
| 4,924,875 A | 5/1990 | Chamoun | |
| 5,007,427 A | 4/1991 | Suzuki et al. | |

(Continued)

FOREIGN PATENT DOCUMENTS

| | | |
|---|---|---|
| CA | 2459408 A1 | 3/2003 |
| EP | 0879618 A1 | 11/1998 |

(Continued)

OTHER PUBLICATIONS

U.S. Appl. No. 10/788,906, Response filed Sep. 11, 2008 to Non Final Office Action mailed Jun. 11, 2008, 24 pgs.

(Continued)

*Primary Examiner* — Carl H Layno
*Assistant Examiner* — Luther Behringer
(74) *Attorney, Agent, or Firm* — Schwegman Lundberg & Woessner, P.A.

(57) ABSTRACT

A gene regulatory system detects ischemia events and is capable of delivering a biologic therapy in response to the detection of an ischemic event or the reception of a command. The biologic therapy protects the heart from ischemic damage by regulating the expression of an exogenously introduced gene product. In one embodiment, the gene regulatory system includes an implantable system that emits at least one gene regulatory signal in response to the detection of the ischemic event or the reception of the command. The gene regulatory signal directly or indirectly regulates gene expression of the gene product.

20 Claims, 7 Drawing Sheets

(56) References Cited

U.S. PATENT DOCUMENTS

| | | |
|---|---|---|
| 5,020,540 A | 6/1991 | Cahmoun |
| 5,025,786 A | 6/1991 | Siegel |
| 5,054,496 A | 10/1991 | Wen et al. |
| 5,072,458 A | 12/1991 | Suzuki |
| 5,103,821 A | 4/1992 | King |
| 5,111,818 A | 5/1992 | Suzuki et al. |
| 5,130,141 A | 7/1992 | Law et al. |
| 5,199,428 A | 4/1993 | Obel et al. |
| 5,228,449 A | 7/1993 | Christ et al. |
| 5,259,380 A | 11/1993 | Mendes et al. |
| 5,282,840 A | 2/1994 | Hudrlik |
| 5,312,453 A | 5/1994 | Shelton et al. |
| 5,314,430 A | 5/1994 | Bardy |
| 5,334,221 A | 8/1994 | Bardy |
| 5,376,106 A | 12/1994 | Stahmann et al. |
| 5,485,849 A | 1/1996 | Panescu et al. |
| 5,486,359 A | 1/1996 | Caplan et al. |
| 5,505,202 A | 4/1996 | Mogi et al. |
| 5,520,191 A | 5/1996 | Karlsson et al. |
| 5,543,318 A | 8/1996 | Smith et al. |
| 5,571,151 A | 11/1996 | Gregory |
| 5,580,779 A | 12/1996 | Smith et al. |
| 5,610,172 A | 3/1997 | Weidmann et al. |
| 5,792,066 A | 8/1998 | Kwong |
| 5,819,741 A | 10/1998 | Karlsson et al. |
| 5,824,021 A | 10/1998 | Rise |
| 5,833,621 A | 11/1998 | Panescu et al. |
| 5,865,787 A | 2/1999 | Shapland et al. |
| 5,891,045 A | 4/1999 | Albrecht et al. |
| 5,902,324 A | 5/1999 | Thompson et al. |
| 6,005,009 A | 12/1999 | Murad et al. |
| 6,021,350 A | 2/2000 | Mathson |
| 6,038,469 A | 3/2000 | Karlsson et al. |
| 6,047,206 A | 4/2000 | Albrecht et al. |
| 6,066,094 A | 5/2000 | Ben-Haim |
| 6,083,930 A | 7/2000 | Roufa et al. |
| 6,090,622 A | 7/2000 | Gearhart et al. |
| 6,108,577 A | 8/2000 | Benser |
| 6,112,116 A | 8/2000 | Fischell et al. |
| 6,119,554 A | 9/2000 | Plankenhorn |
| 6,151,525 A | 11/2000 | Soykan et al. |
| 6,171,256 B1 | 1/2001 | Joo et al. |
| 6,217,525 B1 | 4/2001 | Medema et al. |
| 6,233,486 B1 | 5/2001 | Ekwall et al. |
| 6,245,566 B1 | 6/2001 | Gearhart et al. |
| 6,272,379 B1 | 8/2001 | Fischell et al. |
| 6,319,205 B1 | 11/2001 | Goor et al. |
| 6,381,493 B1 | 4/2002 | Stadler et al. |
| 6,408,208 B1 | 6/2002 | Sun |
| 6,423,705 B1 | 7/2002 | Tracey et al. |
| 6,436,672 B1 | 8/2002 | Tomlinson |
| 6,463,323 B1 | 10/2002 | Conrad-Vlasak et al. |
| 6,468,263 B1 | 10/2002 | Fischell et al. |
| 6,468,985 B1 | 10/2002 | Huang |
| 6,501,983 B1 | 12/2002 | Natarajan et al. |
| 6,514,195 B1 | 2/2003 | Ferek |
| 6,596,745 B2 | 7/2003 | Gall |
| 6,604,000 B2 | 8/2003 | Lu |
| 6,610,713 B2 | 8/2003 | Tracey |
| 6,610,716 B2 | 8/2003 | Wagle et al. |
| 6,628,987 B1 | 9/2003 | Hill et al. |
| 6,628,988 B2 | 9/2003 | Kramer et al. |
| 6,660,737 B2 | 12/2003 | Almstead et al. |
| 6,666,826 B2 | 12/2003 | Salo et al. |
| 6,702,720 B2 | 3/2004 | Dardik |
| 6,721,591 B2 | 4/2004 | Wei et al. |
| 6,733,996 B2 | 5/2004 | Froehlich et al. |
| 6,759,236 B1 | 7/2004 | Fung et al. |
| 6,768,919 B2 | 7/2004 | Starobin et al. |
| 6,783,979 B2 | 8/2004 | Rosen et al. |
| 6,801,805 B2 | 10/2004 | Stokes et al. |
| 6,810,286 B2 | 10/2004 | Donovan et al. |
| 6,838,471 B2 | 1/2005 | Tracey |
| 6,845,267 B2 | 1/2005 | Harrison et al. |
| 6,849,611 B2 | 2/2005 | Rosen et al. |
| 6,865,420 B1 | 3/2005 | Kroll |
| 6,892,095 B2 | 5/2005 | Salo |
| 6,919,207 B2 | 7/2005 | Goodman et al. |
| 6,937,899 B2 | 8/2005 | Sheldon et al. |
| 7,010,345 B2 | 3/2006 | Hill et al. |
| 7,039,462 B2 | 5/2006 | Pastore et al. |
| 7,072,711 B2 | 7/2006 | Girouard et al. |
| 7,181,268 B2 | 2/2007 | Sheldon et al. |
| 7,181,269 B1 | 2/2007 | Kroll |
| 7,190,996 B2 | 3/2007 | Jarverud |
| 7,215,992 B2 | 5/2007 | Stahmann et al. |
| 7,369,892 B2 | 5/2008 | Ferek-Petric |
| 7,400,931 B2 | 7/2008 | Mandrusov et al. |
| 7,415,307 B2 | 8/2008 | Sharma et al. |
| 7,512,439 B1 | 3/2009 | Farazi |
| 7,539,533 B2 | 5/2009 | Tran |
| 7,577,478 B1 | 8/2009 | Kroll et al. |
| 7,736,319 B2 | 6/2010 | Patangay et al. |
| 7,764,995 B2 | 7/2010 | Girouard et al. |
| 7,774,057 B2 | 8/2010 | Pastore et al. |
| 7,780,606 B2 | 8/2010 | Carlson et al. |
| 7,840,263 B2 | 11/2010 | Girouard et al. |
| 7,885,710 B2 | 2/2011 | Sih et al. |
| 7,894,896 B2 | 2/2011 | Baynham et al. |
| 7,917,210 B2 | 3/2011 | Baynham et al. |
| 8,396,552 B2 | 3/2013 | Baynham et al. |
| 2002/0010492 A1 | 1/2002 | Donovan et al. |
| 2002/0019350 A1 | 2/2002 | Levine et al. |
| 2002/0022022 A1 | 2/2002 | Shi et al. |
| 2002/0031827 A1 | 3/2002 | Kanno et al. |
| 2002/0042632 A1 | 4/2002 | Iaizzo et al. |
| 2002/0049154 A1 | 4/2002 | Grissom et al. |
| 2002/0065243 A1 | 5/2002 | Fung et al. |
| 2002/0072777 A1 | 6/2002 | Lu |
| 2002/0072785 A1 | 6/2002 | Nelson et al. |
| 2002/0099026 A1 | 7/2002 | Goodman et al. |
| 2002/0107553 A1 | 8/2002 | Hill et al. |
| 2002/0110910 A1 | 8/2002 | Gwathmey et al. |
| 2002/0111551 A1 | 8/2002 | Van Erlach et al. |
| 2002/0120205 A1 | 8/2002 | Ferek-Petric |
| 2002/0123772 A1 | 9/2002 | Sun et al. |
| 2002/0124855 A1 | 9/2002 | Chachques |
| 2002/0143369 A1 | 10/2002 | Hill et al. |
| 2002/0147329 A1 | 10/2002 | Luyten et al. |
| 2002/0155101 A1 | 10/2002 | Donahue et al. |
| 2002/0161410 A1 | 10/2002 | Kramer et al. |
| 2002/0172663 A1 | 11/2002 | Palasis |
| 2002/0183686 A1 | 12/2002 | Darvish et al. |
| 2003/0004549 A1 | 1/2003 | Hill et al. |
| 2003/0036773 A1 | 2/2003 | Whitehurst et al. |
| 2003/0040777 A1 | 2/2003 | Shemer et al. |
| 2003/0044802 A1 | 3/2003 | Sayler et al. |
| 2003/0045908 A1 | 3/2003 | Condie et al. |
| 2003/0059463 A1 | 3/2003 | Lahtinen |
| 2003/0060854 A1 | 3/2003 | Zhu |
| 2003/0073235 A1 | 4/2003 | Lagarias et al. |
| 2003/0087264 A1 | 5/2003 | Kaplitt et al. |
| 2003/0087867 A1 | 5/2003 | Vogels et al. |
| 2003/0105493 A1 | 6/2003 | Salo |
| 2003/0130581 A1 | 7/2003 | Salo et al. |
| 2003/0139778 A1 | 7/2003 | Fischell et al. |
| 2003/0144702 A1 | 7/2003 | Yu et al. |
| 2003/0144703 A1 | 7/2003 | Yu et al. |
| 2003/0148351 A1 | 8/2003 | Henry et al. |
| 2003/0148968 A1 | 8/2003 | Hammond et al. |
| 2003/0153952 A1 | 8/2003 | Auricchio et al. |
| 2003/0158584 A1 | 8/2003 | Cates et al. |
| 2003/0167081 A1 | 9/2003 | Zhu et al. |
| 2003/0176798 A1 | 9/2003 | Simon |
| 2003/0199813 A1 | 10/2003 | Struble |
| 2003/0204206 A1 | 10/2003 | Padua et al. |
| 2003/0216476 A1 | 11/2003 | Kleemann |
| 2003/0233130 A1 | 12/2003 | Padmanabhan et al. |
| 2004/0005295 A1 | 1/2004 | Lee et al. |
| 2004/0015081 A1 | 1/2004 | Kramer et al. |
| 2004/0030379 A1 | 2/2004 | Hamm et al. |
| 2004/0038400 A1 | 2/2004 | Froehlich et al. |
| 2004/0048286 A1 | 3/2004 | Lee |
| 2004/0049235 A1 | 3/2004 | Deno et al. |

| | | |
|---|---|---|
| 2004/0071637 A1 | 4/2004 | Elia |
| 2004/0073260 A1 | 4/2004 | Brighton |
| 2004/0088017 A1 | 5/2004 | Sharma et al. |
| 2004/0098075 A1 | 5/2004 | Lee |
| 2004/0102815 A1 | 5/2004 | Balczewski et al. |
| 2004/0106954 A1 | 6/2004 | Whitehurst et al. |
| 2004/0106960 A1 | 6/2004 | Siejko et al. |
| 2004/0122478 A1 | 6/2004 | Stadler et al. |
| 2004/0131601 A1 | 7/2004 | Epstein et al. |
| 2004/0132184 A1 | 7/2004 | Dennis et al. |
| 2004/0132190 A1 | 7/2004 | Dillmann et al. |
| 2004/0133247 A1 | 7/2004 | Stahmann et al. |
| 2004/0158289 A1 | 8/2004 | Girouard et al. |
| 2004/0158290 A1 | 8/2004 | Girouard et al. |
| 2004/0186546 A1 | 9/2004 | Mandrusov et al. |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0005923 A1 | 1/2005 | Herrin |
| 2005/0008628 A1 | 1/2005 | Feld et al. |
| 2005/0021091 A1 | 1/2005 | Laske et al. |
| 2005/0038345 A1 | 2/2005 | Gorgenberg et al. |
| 2005/0043675 A1 | 2/2005 | Pastore et al. |
| 2005/0059153 A1 | 3/2005 | George et al. |
| 2005/0059999 A1 | 3/2005 | Mongeon et al. |
| 2005/0075673 A1 | 4/2005 | Warkentin et al. |
| 2005/0096701 A1 | 5/2005 | Donovan et al. |
| 2005/0096706 A1 | 5/2005 | Salo |
| 2005/0113705 A1 | 5/2005 | Fischell et al. |
| 2005/0118144 A1 | 6/2005 | Zhang |
| 2005/0123526 A1 | 6/2005 | Shafer |
| 2005/0130136 A1 | 6/2005 | Lee |
| 2005/0137483 A1 | 6/2005 | Fischell et al. |
| 2005/0137626 A1 | 6/2005 | Pastore et al. |
| 2005/0137631 A1 | 6/2005 | Yu et al. |
| 2005/0159666 A1 | 7/2005 | Pearce et al. |
| 2005/0192637 A1 | 9/2005 | Girouard et al. |
| 2005/0197674 A1 | 9/2005 | McCabe et al. |
| 2005/0245972 A1 | 11/2005 | Onyekaba et al. |
| 2005/0256417 A1 | 11/2005 | Fischell et al. |
| 2005/0283197 A1 | 12/2005 | Daum et al. |
| 2005/0288721 A1 | 12/2005 | Girouard et al. |
| 2006/0009811 A1 | 1/2006 | Sheldon et al. |
| 2006/0015146 A1 | 1/2006 | Girouard et al. |
| 2006/0030892 A1 | 2/2006 | Kadhiresan et al. |
| 2006/0052717 A1 | 3/2006 | Mugler et al. |
| 2006/0110374 A1 | 5/2006 | Czeiger et al. |
| 2006/0116593 A1 | 6/2006 | Zhang et al. |
| 2006/0134071 A1 | 6/2006 | Ross et al. |
| 2006/0134079 A1 | 6/2006 | Sih et al. |
| 2006/0148737 A1 | 7/2006 | Harmon |
| 2006/0149326 A1 | 7/2006 | Prinzen et al. |
| 2006/0241357 A1 | 10/2006 | Chirife |
| 2006/0247700 A1 | 11/2006 | Jackson |
| 2006/0253044 A1 | 11/2006 | Zhang et al. |
| 2006/0259087 A1 | 11/2006 | Baynham et al. |
| 2006/0259088 A1 | 11/2006 | Pastore et al. |
| 2006/0271119 A1 | 11/2006 | Ni et al. |
| 2006/0287684 A1 | 12/2006 | Baynham et al. |
| 2007/0021789 A1 | 1/2007 | Pastore et al. |
| 2007/0027487 A1 | 2/2007 | Mika et al. |
| 2007/0038256 A1 | 2/2007 | Maschke |
| 2007/0043393 A1 | 2/2007 | Brockway et al. |
| 2007/0054871 A1 | 3/2007 | Pastore et al. |
| 2007/0078507 A1 | 4/2007 | Zacouto |
| 2007/0093720 A1 | 4/2007 | Fischell et al. |
| 2007/0129639 A1 | 6/2007 | Zhang et al. |
| 2007/0150005 A1 | 6/2007 | Sih et al. |
| 2007/0203524 A1 | 8/2007 | Sheldon et al. |
| 2007/0208263 A1 | 9/2007 | John et al. |
| 2007/0239218 A1 | 10/2007 | Carlson et al. |
| 2007/0276453 A1 | 11/2007 | Hill et al. |
| 2007/0299356 A1 | 12/2007 | Wariar et al. |
| 2008/0091138 A1 | 4/2008 | Pastore et al. |
| 2008/0139954 A1 | 6/2008 | Day et al. |
| 2008/0188762 A1 | 8/2008 | John et al. |
| 2008/0188763 A1 | 8/2008 | John et al. |
| 2008/0228094 A1 | 9/2008 | Audet et al. |
| 2008/0287818 A1 | 11/2008 | Shelchuk et al. |
| 2009/0048528 A1 | 2/2009 | Hopenfeld et al. |
| 2009/0082682 A1 | 3/2009 | Fischell et al. |
| 2009/0171228 A1 | 7/2009 | Fischell et al. |
| 2009/0177103 A1 | 7/2009 | Bharmi |
| 2010/0286592 A1 | 11/2010 | Girouard et al. |
| 2011/0077701 A1 | 3/2011 | Sih et al. |
| 2011/0137363 A1 | 6/2011 | Baynham et al. |
| 2011/0144709 A1 | 6/2011 | Baynham et al. |

FOREIGN PATENT DOCUMENTS

| | | |
|---|---|---|
| EP | 1690566 A1 | 8/2006 |
| EP | 1904164 | 5/2011 |
| JP | 7504597 A | 5/1995 |
| JP | 2001501596 A | 2/2001 |
| JP | 2002522103 A | 7/2002 |
| JP | 2004-508110 A | 3/2004 |
| JP | 2004516274 A | 6/2004 |
| JP | 2005501617 A | 1/2005 |
| JP | 2005063332 A | 3/2005 |
| JP | 2005177458 A1 | 7/2005 |
| JP | 2006-5062074 A | 2/2006 |
| JP | 2008539983 A | 11/2008 |
| WO | WO-9400192 | 1/1994 |
| WO | WO-98/08859 A1 | 3/1998 |
| WO | WO-99/25385 A1 | 5/1999 |
| WO | WO0007497 | 2/2000 |
| WO | WO-00/78391 A1 | 12/2000 |
| WO | WO-01/28625 A1 | 4/2001 |
| WO | WO-0220088 A1 | 3/2002 |
| WO | WO-02/49714 A2 | 6/2002 |
| WO | WO-0249669 A2 | 6/2002 |
| WO | WO-2004/045709 A1 | 6/2004 |
| WO | WO-2004/093969 A1 | 11/2004 |
| WO | WO-2005/046790 A2 | 5/2005 |
| WO | WO-2005/084751 A2 | 9/2005 |
| WO | WO-2005/120635 A1 | 12/2005 |
| WO | WO-2006/124636 A2 | 11/2006 |
| WO | WO-2006/124729 A2 | 11/2006 |
| WO | WO-2007/133962 A2 | 11/2007 |
| WO | WO-2008/109040 A2 | 9/2008 |

OTHER PUBLICATIONS

U.S. Appl. No. 10/788,906, Response filed Sep. 26, 2007 to Non-Final Office Action mailed Apr. 26, 2007, 26 pgs.

U.S. Appl. No. 10/788,906, Response filed Oct. 22, 2009 to Non Final Office Action mailed Jun. 22, 2009, 24 pgs.

U.S. Appl. No. 10/788,906, Response filed Oct. 24, 2005 to Restriction Requirement mailed Sep. 23, 2005, 23 pgs.

U.S. Appl. No. 10/788,906, Restriction Requirement mailed Jan. 24, 2006, 4 pgs.

U.S. Appl. No. 10/788,906, Restriction Requirement mailed Apr. 21, 2008, 6 pgs.

U.S. Appl. No. 10/788,906, Restriction Requirement mailed Sep. 23, 2005, 12 pgs.

U.S. Appl. No. 10/788,906, Supplemental Amendment and Response filed Apr. 24, 2007 to Final Office Action mailed Oct. 2, 2006, 25 pgs.

U.S. Appl. No. 10/862,716, Final Office Action mailed Jul. 13, 2007, 16 pgs.

U.S. Appl. No. 10/862,716, Final Office Action mailed Aug. 20, 2008, 6 pgs.

U.S. Appl. No. 10/862,716, Non Final Office Action mailed Sep. 19, 2007, 28 pgs.

U.S. Appl. No. 10/862,716, Non Final Office Action mailed Dec. 14, 2006, 10 pgs.

U.S. Appl. No. 10/862,716, Non-Final Office Action mailed May 1, 2009, 9 pgs.

U.S. Appl. No. 10/862,716, Notice of Allowance mailed Mar. 23, 2010, 4 pgs.

U.S. Appl. No. 10/862,716, Notice of Allowance mailed Dec. 1, 2009, 4 pgs.

U.S. Appl. No. 10/862,716, Response filed Feb. 4, 2009 to Restriction Requirement mailed Dec. 5, 2008, 23 pgs.

U.S. Appl. No. 10/862,716, Response filed Mar. 14, 2007 to Non Final Office Action mailed Dec. 14, 2006, 18 pgs.

U.S. Appl. No. 10/862,716, Response filed May 20, 2008 to Restriction Requirement mailed Apr. 21, 2008, 10 pgs.
U.S. Appl. No. 10/862,716, Response filed Jun. 30, 2009 to Non Final Office Action mailed May 1, 2009, 10 pgs.
U.S. Appl. No. 10/862,716, Response filed Sep. 12, 2007 to Final Office Action mailed Jul. 13, 2007, 24 pgs.
U.S. Appl. No. 10/862,716, Response filed Oct. 12, 2006 to Restriction Requirement mailed Sep. 12, 2006, 18 pgs.
U.S. Appl. No. 10/862,716, Response filed Nov. 19, 2008 to Final Office Action mailed Aug. 20, 2008, 11 pgs.
U.S. Appl. No. 10/862,716, Response filed Dec. 19, 2007 to Non-Final Office Action mailed Sep. 19, 2007, 18 pgs.
U.S. Appl. No. 10/862,716, Restrictiion Requirement mailed Apr. 21, 2008, 5 pgs.
U.S. Appl. No. 10/862,716, Restriction Requirement mailed Sep. 12, 2006, 6 pgs.
U.S. Appl. No. 10/862,716, Restriction Requirement mailed Dec. 5, 2008, 8 pgs.
U.S. Appl. No. 11/113,828, Non-Final Office Action mailed Mar. 5, 2008, 8 pgs.
U.S. Appl. No. 11/129,050, Advisory Action mailed Jul. 14, 2009, 3 pgs.
U.S. Appl. No. 11/129,050, Advisory Action mailed Jul. 28, 2008, 3 pgs.
U.S. Appl. No. 11/129,050, Examiner Interview Summary mailed Feb. 11, 2009, 2 pgs.
U.S. Appl. No. 11/129,050, Final Office Action mailed Apr. 21, 2009, 10 pgs.
U.S. Appl. No. 11/129,050, Final Office Action mailed May 12, 2008, 8 pgs.
U.S. Appl. No. 11/129,050, Non-Final Office Action mailed Nov. 6, 2008, 7 pgs.
U.S. Appl. No. 11/129,050, Non-Final Office Action mailed Nov. 26, 2007, 7 pgs.
U.S. Appl. No. 11/129,050, Notice of Allowance mailed Apr. 1, 2010, 6 pgs.
U.S. Appl. No. 11/129,050, Notice of Allowance mailed Jul. 16, 2010, 4 pgs.
U.S. Appl. No. 11/129,050, Notice of Allowance mailed Aug. 24, 2009, 7 pgs.
U.S. Appl. No. 11/129,050, Notice of Allowance mailed Nov. 1, 2010, 6 pgs.
U.S. Appl. No. 11/129,050, Notice of Allowance mailed Dec. 2, 2009, 4 pgs.
U.S. Appl. No. 11/129,050, Response filed Feb. 23, 2009 to Non-Final Office Action mailed Nov. 6, 2008, 13 pgs.
U.S. Appl. No. 11/129,050, Response filed Feb. 26, 2008 to Non-Final Office Action mailed Nov. 26, 2007, 14 pgs.
U.S. Appl. No. 11/129,050, Response filed Jun. 22, 2009 to Final Office Action mailed Apr. 21, 2009, 9 pgs.
U.S. Appl. No. 11/129,050, Response filed Jul. 14, 2008 to Final Office Action mailed May 12, 2008, 13 pgs.
U.S. Appl. No. 11/129,050, Response filed Sep. 28, 2007 to Restriction Requirement mailed Aug. 1, 2007, 11 pgs.
U.S. Appl. No. 11/129,050, Restriction Requirement mailed Aug. 1, 2007, 6 pgs.
U.S. Appl. No. 11/129,050, Supplemental Amendment and Response filed Sep. 12, 2008 to Final Office Action mailed May 12, 2008 and the Advisory Action mailed Jul. 28, 2008, 12 pgs.
U.S. Appl. No. 11/220,397, Response filed Aug. 27, 2008 to Restriction Requirement mailed Aug. 4, 2008, 8 pgs.
U.S. Appl. No. 11/220,397, Response filed Oct. 21, 2008 to Restriction Requirement mailed Sep. 24, 2008, 44 pgs.
U.S. Appl. No. 11/220,397, Final Office Action mailed May 22, 2009, 12 pgs.
U.S. Appl. No. 11/220,397, Non-Final Office Action mailed Dec. 22, 2008, 14 pgs.
U.S. Appl. No. 11/220,397, Notice of Allowance mailed Mar. 30, 2010, 6 pgs.
U.S. Appl. No. 11/220,397, Notice of Allowance mailed Dec. 3, 2009, 10 pgs.
U.S. Appl. No. 11/220,397, Response filed Mar. 23, 2008 to Non Final Office Action mailed Dec. 22, 2008, 14 pgs.
U.S. Appl. No. 11/220,397, Response filed Aug. 24, 2009 to Final Office Action mailed May 22, 2009, 12 pgs.
U.S. Appl. No. 11/220,397, Restriction Requirement mailed Aug. 4, 2008, 7 pgs.
U.S. Appl. No. 11/220,397, Restriction Requirement mailed Sep. 24, 2008, 6 pgs.
U.S. Appl. No. 11/318,263, Notice of Allowance mailed Sep. 29, 2010, 6 pgs.
U.S. Appl. No. 11/318,263, Non-Final Office Action mailed Aug. 20, 2008, 10 pgs.
U.S. Appl. No. 11/318,263, Response filed May 22, 2008 to Restriction Requirement mailed Apr. 23, 2008, 10 pgs.
U.S. Appl. No. 11/318,263, Response filed Nov. 20, 2008 to Non-Final Office Action mailed Aug. 20, 2008, 12 pgs.
U.S. Appl. No. 11/318,263, Restriction Requirement mailed Apr. 23, 2008, 7 pgs.
U.S. Appl. No. 11/318,263, Final Office Action mailed Mar. 17, 2009, 11 pgs.
U.S. Appl. No. 11/318,263, Non-Final Office Action mailed Nov. 27, 2009, 9 pgs.
U.S. Appl. No. 11/318,263, Response filed Feb. 26, 2010 to Office Action,mailed Nov. 27, 2009, 11 pgs.
U.S. Appl. No. 11/318,263, Response filed Aug. 12, 2009 to Restriction Requirement mailed Jul. 14, 2009, 9 pgs.
U.S. Appl. No. 11/318,263, Response filed May 18, 2009 to Final Office Action mailed Mar. 17, 2009, 12 pgs.
U.S. Appl. No. 11/318,263; Response filed Aug. 2, 2010 to Final Office Action mailed Jun. 3, 2010, 13 pgs.
U.S. Appl. No. 11/318,263, Restriction Requirement mailed Jul. 14, 2009, 5 pgs.
U.S. Appl. No. 11/318,263, Final Office Action mailed Jun. 3, 2010, 11 pgs.
U.S. Appl. No. 11/382,849, Final Office Action mailed Jan. 28, 2010, 7 pgs.
U.S. Appl. No. 11/382,849, Non-Final Office Action mailed May 12, 2010, 5 pgs.
U.S. Appl. No. 11/382,849, Non-Final Office Action mailed Aug. 31, 2009, 8 pgs.
U.S. Appl. No. 11/382,849, Notice of Allowance mailed Oct. 15, 2010, 6 pgs.
U.S. Appl. No. 11/382,849, Response filed Apr. 26, 2010 to Final Office Action mailed Jan. 28, 2010, 10 pgs.
U.S. Appl. No. 11/382,849, Response filed Jun. 8, 2009 to Restriction Requirement mailed May 6, 2009, 8 pgs.
U.S. Appl. No. 11/382,849, Response filed Aug. 2, 2010 to Non Final Office Action mailed May 12, 2010, 7 pgs.
U.S. Appl. No. 11/382,849, Response filed Nov. 30, 2009 to Non Final Office Action mailed Aug. 31, 2009, 11 pgs.
U.S. Appl. No. 11/382,849, Restriction Requirement mailed May 6, 2009, 6 pgs.
U.S. Appl. No. 11/682,448, Final Office Action mailed Oct. 7, 2010, 6 pgs.
U.S. Appl. No. 11/682,448, Non-Final Office Action mailed Apr. 5, 2010, 16 pgs.
U.S. Appl. No. 11/682,448, Response filed Jul. 1, 2010 to Non Final Office Action mailed Apr. 5, 2010, 12 pgs.
Australian Application Serial No. 2008223498, First Examiner Report mailed Aug. 16, 2010, 3 Pgs.
European Application Serial No. 05757159.8, Communication mailed Mar. 16, 2007, 2 pgs.
European Application Serial No. 05757159.8, Office Action received Oct. 29, 2009, 3 pgs.
European Application Serial No. 05757159.8, Response filed Apr. 24, 2007 to Communication mailed Mar. 16, 2007, 16 pgs.
European Application Serial No. 06752527.9, Communication mailed Mar. 8, 2010, 6 pgs.
European Application Serial No. 06752527.9, Office Action Response mailed Jul. 7, 2010, 15 pgs.
European Application Serial No. 06752527.9, Summons to Attend Oral Proceedings Received mailed Jul. 23, 2010, 3 pgs.
European Application Serial No. 06762527.9, Communication pursuant to Rules 161 to 182 EPC mailed Mar. 3, 2008, 2 pgs.

European Application Serial No. 06762527.9, Response filed Apr. 9, 2008 to Communication pursuant to Rules 161 to 182 EPC mailed Mar. 3, 2008, 6 pgs.
European Application Serial No. 07797336.0, Communication dated Dec. 19, 2008, 2 pgs.
European Application Serial No. 07797336.0, Communication mailed Mar. 10, 2010, 3 pgs.
European Application Serial No. 07797336.0, Office Action mailed Feb. 24, 2009, 4 pgs.
European Application Serial No. 07797336.0, Response filed Jul. 6, 2009 to Communication mailed Feb. 24, 2009, 20 pgs.
European Application Serial No. 07797336.0, Response Filed Jul. 7, 2010 to Office Action dated Mar. 10, 2010, 5 pgs.
European Application Serial No. 08726356.2, Office Action mailed May 31, 2010, 7 Pgs.
European Application Serial No. 08726356.2, Response filed Aug. 27, 2010 to Communication dated May 31, 2010, 14 pgs.
International Application No. PCT/US2005/006069, International Search Report and Written Opinion mailed Oct. 20, 2005, 19 pgs.
International Application No. PCT/US2005/019731, International Search Report and Written Opinion mailed Oct. 6, 2005, 15 pgs.
International Application Serial No. PCT/US2006/018497, International Search Report mailed Oct. 24, 2006, 5 pgs.
International Application Serial No. PCT/US2006/018497, Written Opinion mailed Oct. 24, 2006, 7 pgs.
International Application Serial No. PCT/US2007/068217, International Search Report mailed Oct. 30, 2007, 5 pgs.
International Application Serial No. PCT/US2007/068217, Written Opinion mailed Oct. 30, 2007, 8 pgs.
International Application Serial No. PCT/US2008/002799, Invitation to Pay Fees and Partial International Search Report mailed Jul. 14, 2008, 7 pgs.
International Application Serial No. PCT/US2008/002799. International Search Report mailed Oct. 15, 2008, 6 pgs.
International Application Serial No. PCT/US2008/002799, Written Opinion mailed Oct. 15, 2008, 11 pgs.
International Applicaton No. PCT/US2005/006069, Invitation to Pay Additional Fees and Partial International Search Report mailed Jul. 20, 2005, 7 pgs.
Japanese Application Serial No. 2007-501003, Amendment filed Feb. 28, 2008, (w/ English Translation of Claims), 21 pgs.
Japanese Application Serial No. 2007-515663, Amendment filed May 27, 2008, (w/ English Translation of Claims), 19 pgs.
Japanese Application Serial No. 2008-511421, Voluntary Amendment filed Apr. 27, 2009, (w/ English Translation of Amended Claims), 11 pgs.
Japanese Application Serial No. 2009-510093, Voluntary Amendment filed Jan. 14, 2009, 4 pgs.
Japanese Application Serial No. 2009-552705, Amendment filed Oct. 21, 2009, (w/ English Translation), 43 pgs.
Akiyama-Uchida, Y., et al., "Norepinephrine enhances fibrosis mediated by TGF-beta in cardiac fibroblasts", *Hypertension*, 40(2), (Aug. 2002), 148-54.
Aukrust, Pal, et al., "Immunomodulating Therapy: New Treatment Modality in Congestive Heart Failure", *Congest Heart Fail.*, 9(2), (Mar.-Apr. 2003), 64-69.
Baker, A. H., "Development and Use of Gene Transfer for Treatment of Cardiovascular Disease", *J Card Surg*, 17, (2002), 543-548.
Bigatel, D. A., et al., "The matrix metalloproteinase inhibitor BB-94 limits expansion of experimental abdominal aortic aneurysms", *J Vasc Surg*, 29(1), (1999), 130-8.
Birnbaum, Y, et al., "Ischemic preconditioning at a distance: reduction of myocardial infarct size by partial reduction of blood supply combined with rapid stimulation of the gastrocnemius muscle in the rabbit.", *Circulation*, 96(5), (Sep. 7, 1997), 1641-6.
Bovenberg, W. A., et al., "Expression of recombinant human insulin-like growth factor I in mammalian cells", *Mol Cell Endocrinol.*, 74(1), (Nov. 12, 1990), 45-59.
Brugada, R., et al., "Genetics of Cardiovascular Disease with Emphasis on Atrial Fibrillation", *Journal of Interventional Cardiac Electrophysiology*, 3, (1999), 7-13.
Brundel, B. J. M., et al., "Alterations in Potassium Channel Gene Expression in Atria of Patients With Persistent and Paroxysmal Atrial Fibrillation: Differential Regulation of Protein and mRNA Levels for K+ Channels", *Journal of the American College of Cardiology*, 37(3), (2001), 926-932.
Buchwald, A B, et al., "Decoy Oligodeoxynucleotide Against Activator Protein-1 Reduces Neointimal Proliferation After Coronary Angioplasty in Hypercholesterolemic Minipigs", *Journal of the American College of Cardiology*, 39 (4), (Feb. 20, 2002), 732-738.
Burton, D. Y., et al., "The Incorporation of an Ion Channel Gene Mutation Associated with the Long QT Syndrome (Q9E-hMiRPI) in a Plasmid Vector for Site-Specific Arrhythmia Gene Therapy: In Vitro and In Vivo Feasibility Studies", *Human Gene Therapy*, 14, (2003), 907-922.
Capecchi, M. R., "High efficiency transformation by direct microinjection of DNA into cultured mammalian cells.", *Cell*, 22(2 Pt 2), (Nov. 1980), 479-88.
Cheng, C.-F., et al., "Genetic Modifiers of Cardiac Arrhythmias", *TRENDS in Molecular Medicine*, 9(2), (2003), 59-66.
Chu, G., "SV40 DNA transfection of cells in suspension: analysis of efficiency of transcription and translation of T-antigen.", *Gene*, 13(2), (Mar. 1981), 197-202.
Cleland, J. G. F., et al., "Update of Clinical Trials from the American College of Cardiology 2003. Ephesus, Sportif-III, Ascot, Companion, UK-PACE and T-wave Alternans", *The European Journal of Heart Failure*, 5, (2003), 391-398.
Colucci, W. S., "Molecular and Cellular Mechanisms of Myocardial Failure", *Am J Cardiol* 80(11A), (1997), 15L-25L.
Cserjesi, P., et al., "Myogenin Induces the Myocyte-Specific Enhancer Binding Factor MEF-2 Independently of Other Muscle-Specific Gene Products", *Molecular and Cellular Biology*, 11(10), (1991), 4854-4862.
Curiel, D. T., et al., "Adenovirus enhancement of transferrin-polylysine-mediated gene delivery", *Proc Natl Acad Sci USA.*, 88(19), (Oct. 1, 1991), 8850-4.
Del Monte, F., et al., "Targeting Calcium Cycling Proteins in Heart Failure Through Gene Transfer", *The Journal of Physiology*, 546(1), (2002), 49-61.
Del Rio, C. L., et al., "Use of Myocardial Electrical Impedance to Assess the Efficacy of Preconditioning", *IEEE Computers in Cardiology*, (2002), 489-492.
Dhawan, J., et al., "Tetracycline-Regulated Gene Expression Following Direct Gene Transfer into Mouse Skeletal Muscle", *Somatic Cell and Molecular Genetics*, 21(4), (1995), 233-240.
Dobrev, D., et al., "Molecular Basis of Downregulation of G-Protein-Coupled Inward Rectifying K+Current ($I_{k,aCh}$) in Chronic Human Atrial Fibrillation", *Circulation*, 104, (2001), 2551-2557.
Donahue, J. K., et al., "Focal modification of electrical conduction in the heart by viral gene transfer.", *Nat Med.*, 6(12), (Dec. 2000), 1395-1398.
Dzwonczyk, R., et al., "Myocardial electrical impedance responds to ischemia and reperfusion in humans", *IEEE Transactions on Biomedical Engineering*, 51(12), (Dec. 2004), 2206-2209.
Eckardt, L., et al., "Load-induced changes in repolarization: evidence from experimental and clinical data", *Basic Res Cardiol*, 96(4), (2001), 369-380.
ER, F., et al., "Dominant-negative suppression of HCN channels markedly reduces the native pacemaker current $I_f$ and undermines spontaneous beating of neonatal cardiomyocytes.", *Circulation*, 107(3), (Jan. 2003), 485-489.
Felgner, P. L., et al., "Lipofection: A highly efficient, lipid-mediated DNA-transfection procedure", Proc. Natl. Acad. Sci. USA, 84, (Nov. 1987), 7413-7417.
Gould, P. A., et al., "Review of the Current Management of Atrial Fibrillation", *Expert Opinion on Pharmacotherapy*, 4(11), (2003), 1889-1899.
Graham, F. L., "A New Technique for the Assay of Infectivity of Human Adenovirus 5 DNA", *Virology*, 52, (1973), 456-467.
Hafizi, S., et al., "Inhibition of human cardiac fibroblast mitogenesis by blockade of mitogen-activated protein kinase and phosphatidylinositol 3-kinase.", *Cir Exp Pharma Physiol*, 26(7), (Jul. 1999), 511-513.
Hamawy, A. H., et al., "Cardiac Angiogenesis and Gene Therapy: A Strategy for Myocardial Revascularization", *Current Opinion in Cardiology*, 14, (1999), 515-522.

Hammond, H. K., et al., "Regional myocardial downregulation of the inhibitory guanosine triphosphate-binding protein (Gi alpha 2) and beta-adrenergic receptors in a porcine model of chronic episodic myocardial ischemia", *J Clin Res*, 92(6), (1993), 2644-5262.

Higashi, T., et al., "Pharmacological characterization of endothelin-induced rat pulmonary arterial dilatation", *Br J Pharmacol*, 121(4), (1997), 782-6.

Hong, Y. S., et al., "Localized Immunosuppression in the Cardia Allograft Induced by a New Liposome-Mediated IL-10 Gene Therapy",*J. Heart Lung Transplant*, 21, (2002), 1188-1200.

Huq, F., et al., "Session 5: Cellular and Subcellular Basis of Remodeling—Modulating Signalling Pathways in Hypertrophy and Heart Failure by Gene Transfer", *Journal of Cardiac Failure*, 8(6)(Suppl.), (2002), S389-S400.

Jayakumar, J., et al., "Gene Therapy for Myocardial Prevention—Transfection of Donor Hearts With Heat Shock Protein 70 Gene Protects Cardiac Function Against Ischemia-Reperfusion Therapy", *Circulation*, 102 (*Suppl. III*), (2000), III-302-III-306.

Johnson, J. E., et al., "Muscle Creatine Kinase Sequence Elements Regulating Skeletal and Cardiac Muscle Expression in Transgenic Mice", *Molecular and Cellular Biology*, 9(8), (1989), 3393-3399.

Jugdutt, B. I., "Remodeling of the Myocardium and Potential Targets in the Collagen Degradation and Synthesis Pathways", *Current Drug Targets Cardiovascular & Haematological Disorders*, 3, (2003), 1-30.

Kiba, A., et al., "VEGFR-2-specific ligand VEGF-E induces non-edematous hyper-vascularization in mice.", *Biochem Biophys Res Commun.*, 301(2), (Feb. 7, 2003), 371-377.

Kis, A., "Repeated cardiac pacing extends the time during which canine hearts are protected against ischaemia-induced arrhythmias : role of nitric oxide", *Journal of Molecular and Cellular Cardiology*, 31(6), (1999), 1229-1241.

Klein, T. M., "High-Velocity Microprojectiles for Delivering Nucleic Acids into Living Cells", *Nature*, 327, (1987), 70-73.

Koch, W. J., et al., "Gene Transfer of β-Adrenergic Signaling Components for Heart Failure", *Journal of Cardiac Failure*, 8(*6 Suppl*), (2002), S526-S531.

Kodama, I., et al., "Cellular electropharmacology of amiodarone.", *Cardiovas Res*, 35(1), (1997), 13-29.

Kozarsky, K. F., "Gene Therapy for Cardiovascular Disease", *Current Opinion in Pharmacology*, 1, (2001), 197-202.

Krayenbühl, H. P., "Hemodynamics in ischemia. Systolic phase", *Z. Kardiol.*, 73 Suppl 2, [Article in German with English Abstract], (1984), 119-125.

Lee, L. Y., et al., "Exogenous control of cardiac gene therapy: evidence of regulated myocardial transgene expression after adenovirus and adeno-associated virus transfer of expression cassettes containing corticosteroid response element promoters.", *J Thorac Cardiovasc Surg.*, 118(1), (Jul. 1999), 26-24, discussion 34-35.

Lijnen, P. J., et al., "Induction of Cardiac Fibrosis by Transforming Growth Factor-$\beta_1$", *Molecular Genetics and Metabolism*, 71, (2000), 418-435.

Lin, H., et al., "Regulating genes with electromagnetic response elements", *Journal of Cellular Biochemistry*, 81(1), (2001), 143-148.

Lin, H., et al., "Specific region of the c-myc promoter is responsive to electric and magnetic fields", *Journal of Cellular Biochemistry*, 54(3), (Mar. 1994), 281-288.

Loukogeorgakis, S. P., et al., "Remote ischemic preconditioning provides early and late protection against endothelial ischemia-reperfusion injury in humans: role of the autonomic nervous system. ", *J Am Coll Cardiol.* 46(3), (Aug. 2, 2005), 450-456.

Luttun, A., et al., "The Role of Proteinases in Angiogenesis, Heart Development, Restenosis, Atherosclerosis, Myocardial Ischemia, and Stroke: Insights from Genetic Studies", *Current Atherosclerosis Reports*, 2, (2000), 407-416.

MacGowan, G. A., et al., "New molecular insights into heart failure and cardiomyopathy: potential strategies and therapies", *Ir J Med Sci.*, 171(2), (Apr.-Jun. 2002), 99-104.

MacKenna, Deidre, et al., "Role of mechanical factors in modulating cardia fibroblast function and extracellular matrix synthesis", *Cardiovascular Research*, 46, (2000), 257-263.

MacNeill, MD, B. D., et al., "Targeting Signaling Pathways in Heart Failure by Gene Transfer", *Current Atherosclerosis Reports*, 5, (2003), 178-185.

Mader, S., "A steroid-inducible promoter for the controlled overexpression of cloned genes in eukaryotic cells", *Proc Natl Acad Sci USA*, 90(12), (1993), 5603-7.

Mannino, R. J., "Liposome mediated gene transfer.", *BioTechniques*, 6(7), (Jul.-Aug. 1988), 682-90.

Marban, E., et al., "Gene Therapy for Cardiac Arrhythmias", *Cold Spring Harbor Symposia on Quantitative Biology*, vol. LXVII—*The Cardiovascular System*, Published by Cold Spring Harbor Laboratory Press, (2002), 527-531.

Mbai, M., et al., "Genetic Basis for the Origin of Cardiac Arrhythmias: Implications for Therapy",*Current Cardiology Reports*, 4, (2002), 411-417.

Melo, L. G., et al., "Molecular and cell-based therapies for protection, rescue, and repair of ischemic myocardium: reasons for cautious optimism.", *Circulation*, 109(20), (May 2004), 2386-93.

Miller, L. W., et al., "Limitations of Current Medical Therapies for the Treatment of Heart Failure", *Reviews in Cardiovascular Medicine*, 4(Suppl. 2), (2003), S21-S29.

Murry, C. E., et al., "Preconditioning with ischemia: a delay of lethal cell injury in ischemic myocardium", *Circulation*, 74(5), (1986), 1124-1136.

Muscat, G. E. O., et al., "Multiple 5'-Flanking Regions of the Human alpha-Skeletal Actin Gene Synergistically Modulate Muscle-Specific Expression", *Molecular and Cellular Biology*, 7(11), (1987), 4089-4099.

Nuss, H. B., et al., "Reversal of Potassium Channel Deficiency in Cells from Failing Hearts by Adenoviral Gene Transfer: A Prototype for Gene Therapy for Disorders of Cardiac Excitability and Contractility", *Gene Therapy*, 3(10), (1996), 900-912.

Palermo, J., "Transgenic remodeling of the contractile apparatus in the mammalian heart", *Circ Res*, 78(3), (1996), 504-9.

Patberg, K. W, et al., "Cardiac memory is associated with decreased levels of the transcriptional factor CREB modulated by angiotensin II and calcium.", *Circulation Research*, 93(5), (Sep. 5, 2003), 472-478.

Pouleur, H., et al., "Changes in plasma renin activity and haemodynamics during vasodilator therapy in conscious dogs with myocardial infarction or chronic volume overload", *Eur J Clin Investig*, 13(4), 1983 , 331-338.

Pouzet, B., et al., "Intramyocardial transplantation of autologous myoblasts: can tissue processing be optimized?", *Circulation*, 102(19 Suppl 3), (2000), III-210-III-215.

Prinzen, F. W, et al., "Mapping of Regional Myocardial Strain and Work During Ventricular Pacing: Experimental Study Using Magnetic Resonance Imaging Tagging", *Journal of American College of Cardiology*, 33(6), (1999), 1735-1742.

Qu, J, et al., "HCN2 overexpression in newborn and adult ventricular myocytes: distinct effects on gating and excitability", *Circ. Res.*, vol. 89(1), (Jul. 6, 2001), e8-e14.

Recer, P., "Researchers find first heart attack gene", *AP Science News, Science*:www.science.org, (2003), 1 pg.

Rinsch, C., et al., "Delivery of FGF-2 but not VEGF by encapsulated genetically engineered myoblasts improves survival and vascularization in a model of acute skin flap ischemia", *Gene Therapy*, 8, (2001), 523-533.

Roberts, R., et al., "Genetic Aspects of Arrhythmias", *American Journal of Medical Genetics (Semin. Med. Genet.)*, 97, (2000), 310-318.

Rosa, A., et al., "Ectopic Pacing at Physiological Rate Improves Postanoxic Recovery of the Developing Heart", *Am. J. Physiol.—Heart Circ. Physiol.*, 284, (2003), H2384-H2392.

Roth, D. A., et al., "Downregulation of cardiac guanosine 5'-triphosphate-binding proteins in right atrium and left ventricle in pacing-induced congestive heart failure", *J Clin Invest.*, 91(3), (Mar. 1993), 939-949.

Rubenstrunk, A., et al., "Transcriptional activation of the metallothionein I gene by electric pulses in vivo: basis for the development of a new gene switch system.", The *Journal of Gene Medicine*, 5(9), (Sep. 2003), 773-783.

Rutanen, J., et al., "Progress and Prospects—Post-Intervention Vessel Remodeling", *Gene Therapy*, 9, (2002), 1487-1491.

Sam, F., et al., "Role of Endothelin-1 in Myocardial Failure", *Proceedings of the Association of American Physicians*, 111(5), (1999), 417-422.

Schoemaker, R. G., et al., "Bradykinin mediates cardiac preconditioning at a distance", *Am J Physiol Heart Circ Physiol.*, 278(5), (May 2000), H1571-H1576.

Schram, G., et al., "Differential Distribution of Cardiac Ion Channel Expression as a Basis for Regional Specialization in Electrical Function", *Circulation Research*, 90, (2002), 939-950.

Semenza, G. L., et al., "Hypoxia-inducible nuclear factors bind to an enhancer element located 3' to the human erythropoietin gen", *Proc Natl Acad Sci USA*, 88(13), (1991), 5680-5684.

Semenza, G. L., et al., "Transcriptional Regulation of Genes Encoding Glycolytic Enzymes by Hypoxia-Inducible Factor 1", *The Journal of Biological Chemistry*, 269(38), (1994), 23757-23763.

Shigekawa, K., "Electroporation of Eukaryotes and Prokaryotes: A General Approach to the Introduction of Macromolecules into Cells", *BioTechniques*, 6, (1988), 742-751.

Shockett, P., et al., "A modified Tetracycline-Regulated System Provides Autoregulatory, Inducible Gene Expression in Cultured Cells and Transgenic Mice", *Proc Natl Acad Sci USA*, 92(14), (1995), 6522-6526.

Sukenaga, Y., et al., "Development of the chymase inhibitor as an anti-tissue-remodeling drug: myocardial infarction and some other possibilities", *Jap J Pharmacol*, 90(3), (2002), 218-22.

Taylor, D. A., et al., "Delivery of primary autologous skeletal myoblasts into rabbit heart by coronary infusion: a potential approach to myocardial repair", *Proc Assoc Am Phys*, 109(3), (May 1997), 245-53.

Thijssen, V. J. L., et al., "Analysis of Altered Gene Expression During Sustained Atrial Fibrillation", *Cardiovascular Research*, 54, (2002), 427-437.

Tomaselli, F., et al., "Photodynamic Therapy Enhanced by Hyperbaric Oxygen in Acute Endoluminal Palliation of Malignant Bronchial Stenosis (Clinical Pilot Study in 40 Patients)", European Journal of Cardio-thoracic Surgery, 19, (2001), 549-554.

Towbin, J. A., et al., "Chapter 3—Genetics and Cardiac Arrhythmias", In Advances in Pediatrics, vol. 29, Published by Mosby, Inc., (2002), 87-129.

Van Gelder, MD, I. C., et al., "Alterations in Gene Expression of Proteins Involved in the Calcium Handling in Patients with Atrial Fibrillation", *J Cardiovasc Electrophysical*, 10, (1999), 552-560.

Villarreal, F. J., et al., "Human cardiac fibroblasts and receptors for angiotensin II and bradykinin: A potential role for bradykinin in the modulation of cardiac extracellular matrix", *Basic Research in Cardiology*, 93 Supp 3, (1998), s004-s007.

Walter, Dirk H., et al., "Endothelial progenitor cells: regulation and contribution to adult neovascularization", *Herz*, 27(7), (2002), 579-588.

Walther, W., et al., "Cell Type Specific and Inducible Promoters for Vectors in Gene Therapy as an Approach for Cell Targeting", *Journal of Molecular Medicine*, 74, (1996), 379-392.

Wang, G. L., et al., "Molecular basis of hypoxia-induced erythropoietin expression", *Curr Opin Hematol.*, 3(2), Mar. 1996, 156-162.

Wang, L., et al., "Mutation of MEF2A in an inherited disorder with features of coronary artery disea", *Science* 302(5650), (Nov. 28, 2003), 1578-81.

Wattanapitayakul, S. K., et al., "Recent Developments in Gene Therapy for Cardiac Disease", *Biomedical & Pharmacotherapy*, 54, (2000), 487-504.

Weintraub, H., "The *myoD* Gene Family: Nodal Point During Specification of the Muscle Cell Lineage", *Science*, 251(4995), (1991), 761-766.

Wurm, F. M., et al., "Inducible Overproduction of the Mouse c-myc Protein in Mammalian Cells", *Proc Natl Acad Sci USA.*, 83(15), (Aug. 1986), 5414-5418.

Wyman, T, et al., "Promoter-Activated Expression of Nerve Growth Factor for Treatment of Neurodegenerative Diseases", *Gene Therapy*, 6, (1999), 1648-1660.

Yagi, A., et al., "Anti-inflammatory constituents, aloesin and aloemannan in Aloe species and effects of tanshinon VI in *Salvia miltiorrhiza* on heart", *J Pharm Soc Japan*, 123(7), (Jul. 2003), 517-32.

Zhi-Qing, Z., et al., "Inhibition of myocardial injury by ischemic postconditioning during reperfusion: comparision with ischemic preconditioning", *Am J Physiol Heart Circ Physiol*, 285(2), (2003), H579-H588.

Zimmermann, W. H., et al., "Tissue engineering of a differentiated cardiac muscle construct", *Circulation Res.*, 90(2), (2002), 223-30.

Zou, Y., et al., "Heat Shock Transcription Factor 1 Protects Cardiomyocytes From Ischemia/Reperfusion Injury", *Circulation*, 108 (24), (2003), 3024-3030.

U.S. Appl. No. 10/788,906, Response filed Apr. 19, 2007 to Final Office Action mailed Oct. 2, 2006, 25 pgs.

U.S. Appl. No. 10/788,906, Examiner Interview Summary mailed Mar. 18, 2010, 2 pgs.

U.S. Appl. No. 10/788,906, Examiner Interview Summary mailed Apr. 23, 2007, 3 pgs.

U.S. Appl. No. 10/788,906, Examiner Interview Summary mailed Jun. 11, 2008, 2 pgs.

U.S. Appl. No. 10/788,906, Final Office Action mailed Mar. 18, 2010, 9 pgs.

U.S. Appl. No. 10/788,906, Final Office Action mailed Oct. 2, 2006, 21 pgs.

U.S. Appl. No. 10/788,906, Final Office Action mailed Dec. 4, 2007, 18 pgs.

U.S. Appl. No. 10/788,906, Final Office Action mailed Dec. 10, 2008, 15 pgs.

U.S. Appl. No. 10/788,906, Non Final Office Action mailed Mar. 31, 2006, 22 pgs.

U.S. Appl. No. 10/788,906, Non Final Office Action mailed Apr. 26, 2007, 23 pgs.

U.S. Appl. No. 10/788,906, Non-Final Office Action mailed Mar. 31, 2006, 23 pgs.

U.S. Appl. No. 10/788,906, Non-Final Office Action mailed Jun. 11, 2008, 14 pgs.

U.S. Appl. No. 10/788,906, Non-Final Office Action mailed Jun. 22, 2009, 9 pgs.

U.S. Appl. No. 10/788,906, Notice of Allowance mailed Jul. 14, 2010, 5 pgs.

U.S. Appl. No. 10/788,906, Response filed Feb. 20, 2008 to Final Office Action mailed Dec. 4, 2007, 26 pgs.

U.S. Appl. No. 10/788,906, Response filed Feb. 24, 2006 to Restriction Requirement mailed Jan. 24, 2006, 23 pgs.

U.S. Appl. No. 10/788,906, Response filed Mar. 8, 2007 to Final Office Action mailed Oct. 2, 2006, 25 pgs.

U.S. Appl. No. 10/788,906, Response filed Apr. 9, 2009 to Final Office Action mailed Dec. 10, 2008, 24 pgs.

U.S. Appl. No. 10/788,906, Response filed May 21, 2008 to Restriction Requirement mailed Apr. 21, 2008, 23 pgs.

U.S. Appl. No. 10/788,906, Response filed Jun. 18, 2010 to Final Office Action mailed Mar. 18, 2010, 15 pgs.

U.S. Appl. No. 10/788,906, Response filed Jun. 30, 2006 to Non Final Office Action mailed Mar. 31, 2006, 26 pgs.

U.S. Appl. No. 11/318,263, Advisory Action mailed Aug. 8, 2010, 3 pgs.

U.S. Appl. No. 12/843,524, Non Final Office Action mailed Jun. 10, 2011, 14 pgs.

Japanese Application Serial No. 2007-501003, Office Action mailed Nov. 8, 2010, (w/ English Translation), 5 pgs.

Japanese Application Serial No. 2007-501003, Response filed Feb. 4, 2011 to Office Action mailed Nov. 8, 2010, (w/ English Translation of Amended Claims), 20 pgs.

Japanese Application Serial No. 2007-501003, Office Action mailed May 24, 2011, (w/ English Translation), 3 pgs.

Japanese Application Serial No. 2007-515663, Office Action mailed May 24, 2011, (w/ English Translation), 5 pgs.

U.S. Appl. No. 12/843,524, Response filed Aug. 23, 2011 to Non Final Office Action mailed Jun. 10, 2011, 10 pgs.

U.S. Appl. No. 12/843,524, Final Office Action mailed Oct. 26, 2011, 13 pgs.

Japanese Application Serial No. 2007-501003, Response Filed Sep. 28, 2011 to Final Office Action mailed May 31, 2011, 22 pgs.

Japanese Application Serial No. 2007-515663, Response filed Aug. 17, 2011 to Office Action dated May 24, 2011, (w/ English Translation of Amended Claims), 13 pgs.

U.S. Appl. No. 12/843,524, Response filed Jan. 26, 2012 to Final Office Action mailed Oct. 26, 2011, 10 pgs.

U.S. Appl. No. 13/019,888, Restriction Requirement mailed Apr. 2, 2012, 5 pgs.

U.S. Appl. No. 13/029,631, Non Final Office Action mailed Apr. 12, 2012, 7 pgs.

Japanese Application Serial No. 2007-501003, Office Action after Appeal mailed Mar. 8, 2012, w/ English Translation, 8 pgs.

Japanese Application Serial No. 2007-515663, Office Action mailed Nov. 14, 2011, (w/ English Translation), 5 pgs.

Japanese Application Serial No. 2007-515663, Response filed Feb. 7, 2012 to Office Action mailed Nov. 14, 2011, (w/ Engiish Translation of Amended Claims), 14 pgs.

Japanese Application Serial No. 2008-511421, Office Action mailed Nov. 16, 2011, (w/ English Translation), 5 pgs.

Japanese Application Serial No. 2008-511421, Response filed Mar. 14, 2012 to Office Action mailed Nov. 16, 2011, (w/ English Translation of Amended Claims), 16 pgs.

Japanese Application Serial No. 2009-510093, Office Action mailed Mar. 12, 2012, (w/ English Translation), 9 pgs.

Cohn, JN, et al., "Cardiac remodeling—concepts and clinical implications: a consensus paper from an international forum on cardiac remodeling. Behalf of an International Forum on Cardiac Remodeling.", J Am Coll Cardiol. Mar. 1, 2000:35(3)., Abstract.

Kis, A., et al., "Repeated Cardiac Pacing Extends the Time During Which Canine Hearts are Protected Against Ischaemia-induced Arrhythmias: Role of Nitric Oxide", Journal of Molecular and Cellular, 31(6), (1999), 1229-1241.

U.S. Appl. No. 13/019,888, Non Final Office Action mailed Jun. 29, 2012, 9 pgs.

U.S. Appl. No. 13/019,888, Notice of Allowance mailed Nov. 6, 2012, 8 pgs.

U.S. Appl. No. 13/019,888, Response filed May 2, 2012 to Restriction Requirement mailed Apr. 2, 2012, 8 pgs.

U.S. Appl. No. 13/019,888, Response filed Sep. 28, 2012 to Non Final Office Action mailed Jun. 29, 2012, 10 pgs.

U.S. Appl. No. 13/029,631, Notice of Allowance mailed Aug. 24, 2012, 7 pgs.

U.S. Appl. No. 13/029,631, Response filed Jul. 10, 2012 to Non Final Office Action mailed Apr. 12, 2012, 8 pgs.

Japanese Application Serial No. 2009-510093, Response filed Jun. 11, 2012 to Office Action mailed Mar. 12, 2012, English Claims with response, 11 pgs.

METHOD AND APPARATUS FOR DEVICE CONTROLLED GENE EXPRESSION FOR CARDIAC PROTECTION

CROSS-REFERENCE TO RELATED APPLICATIONS

This application is a divisional of U.S. application Ser. No. 11/220,397, filed Sep. 6, 2005, now issued as U.S. Pat. No. 7,774,057, which is hereby incorporated by reference in its entirety.

This application is related to, commonly assigned U.S. patent application Ser. No. 10/788,906, entitled "METHOD AND APPARATUS FOR DEVICE CONTROLLED GENE EXPRESSION," filed on Feb. 27, 2004, now issued as U.S. Pat. No. 7,840,263, U.S. patent application Ser. No. 10/862,716, entitled "METHOD AND APPARATUS TO MODULATE CELLULAR REGENERATION POST MYOCARDIAL INFARCT," filed on Jun. 7, 2004, now issued as U.S. Pat. No. 7,764,995, and U.S. patent application Ser. No. 11/129,050, entitled "METHOD AND APPARATUS FOR CARDIAC PROTECTION PACING," filed on May 13, 2005, now issued as U.S. Pat. No. 7,917,210, which are hereby incorporated by reference in their entirety.

TECHNICAL FIELD

This document relates generally to gene therapy and particularly, but not by way of limitation, to a system for regulation of gene expression for cardiac protection using a device generating gene transcription triggering signals.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions result from contractions of the myocardium. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony to result in efficient pumping functions. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of myocardial tissue resulting from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

Therefore, there is a need to protect the myocardium from injuries associated with ischemic events, including MI.

SUMMARY

The invention provides a gene regulatory system that detects ischemia events and is capable of delivering a signal to control a biologic therapy in response to the detection of an ischemic event, which biologic therapy protects the heart from potential or further ischemic damage. For example, the present invention provides spatial, temporal and/or conditional control of gene expression from one or more gene therapy vectors introduced (administered) to an animal, including a mammal such as a human, via an implantable device in the animal. The device may be introduced to the animal before, concurrent with or after the gene therapy vector(s) is/are administered. The gene therapy vector includes one or more gene sequences useful to prevent, inhibit or treat ischemia, e.g., prevent, inhibit or treat damage or dysfunction of tissue resulting from a restriction in blood supply to that tissue. In particular, the gene therapy vector includes an open reading frame for a gene product or a portion thereof, i.e., a portion that encodes a gene product with substantially the same activity, e.g., at least 80%, 90% or more of the activity, as the full length gene product, e.g., a full length polypeptide or a glycosylated product thereof, operably linked to at least one regulatable transcriptional control element (an "expression cassette"), the expression of which open reading frame in, for instance, myocardial cells in an animal, is effective to prevent, inhibit or treat ischemia. In one embodiment, the vector(s) which are administered to an animal are not associated with an intact cell ("acellular"), e.g., the vector may be a recombinant virus or isolated nucleic acid having a desirable gene sequence. In another embodiment, recombinant cells which include the gene therapy vector(s) are employed. Optionally, a combination of gene therapy vectors, each with a different open reading frame, at least one of which includes a regulatable transcriptional control element, is employed.

Thus, in one embodiment, a mammal at risk of a myocardial ischemic event is subjected to gene therapy. The gene therapy vector may be administered by any route and, in one embodiment, is administered to myocardial tissue. The gene therapy includes an expression cassette with at least one regulatable transcriptional control element, e.g., an inducible promoter or enhancer, linked to a sequence that encodes at least one therapeutic gene product, the expression of which in the mammal prevents, inhibits or treats myocardial ischemia. For instance, the enhancer may be a glucocorticoid responsive enhancer or the promoter may be an electromagnetic, electric current or light responsive (e.g., inducible) promoter. Prior to, concurrent with or after gene therapy, an implantable device which regulates expression of the gene(s) in the gene therapy vector, is provided to the mammal. In one embodiment, the device is introduced at or near damaged cardiac tissue. In response to detection of an ischemic event, e.g., a change in a physiological parameter such as heart rate, the device emits a signal which activates the regulatable transcriptional control element in the gene therapy vector. Such signals include, but are not limited to, an electric field, electromagnetic field, light, sound, temperature, and/or chemical agents such as a biologic agent (i.e., one encoded by DNA) or a nonbiologic agent, e.g., a beta adrenergic blocker, an alpha adrenergic blocker, a calcium channel blocker, an ACE inhibitor or an angiotension II blocker. Gene expression may be turned on and off by controlling signals emitted by the device.

In one embodiment, a gene regulatory system includes a sensing circuit, an ischemia detector, a gene regulatory signal delivery device, and a controller. The sensing circuit senses one or more physiological parameters (physiological signals), or senses a change in one or more physiological parameters, indicative of an ischemic event. The ischemia detector detects the ischemic event from the one or more parameters or a change therein. The gene regulatory signal delivery device emits at least one gene regulatory signal that directly or indirectly regulates a regulatable transcriptional control element in a gene therapy vector. The controller initiates and controls the emission of the gene regulatory signal in response to the detection of the ischemic event and/or an external command. The amount (strength) and/or duration of the signal alters expression, e.g., induces expression, of the open reading frame in the expression cassette in the gene therapy vector. Thus, the systems and methods of the invention which employ sensors and diagnostic information allow for control of gene therapy.

The invention thus provides a method to control expression of at least one exogenously introduced expression cassette, which includes a regulatable transcriptional control element operably linked to an open reading frame, in an animal at risk of ischemia or in response to an ischemic event in an animal. The method is employed with an animal subjected to gene therapy and having a gene regulatory system of the invention, e.g., a system which includes a sensor to sense a physiological parameter indicative of ischemia, an ischemia detector coupled to the sensor, and a controller coupled to the detector and to a gene regulatory signal delivery device that emits a regulatory signal which directly or indirectly regulates expression of a regulatable transcriptional control element in the gene therapy vector. The controller is adapted to control the emission of the regulatory signal based on the sensed physiological parameter and/or an external command. In one embodiment, in response to detection of an ischemic event, one or more signals, each of a particular strength and duration are emitted (delivered) from the gene regulatory signal delivery device in the animal, optionally followed by periods where the signal is not emitted (not delivered).

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
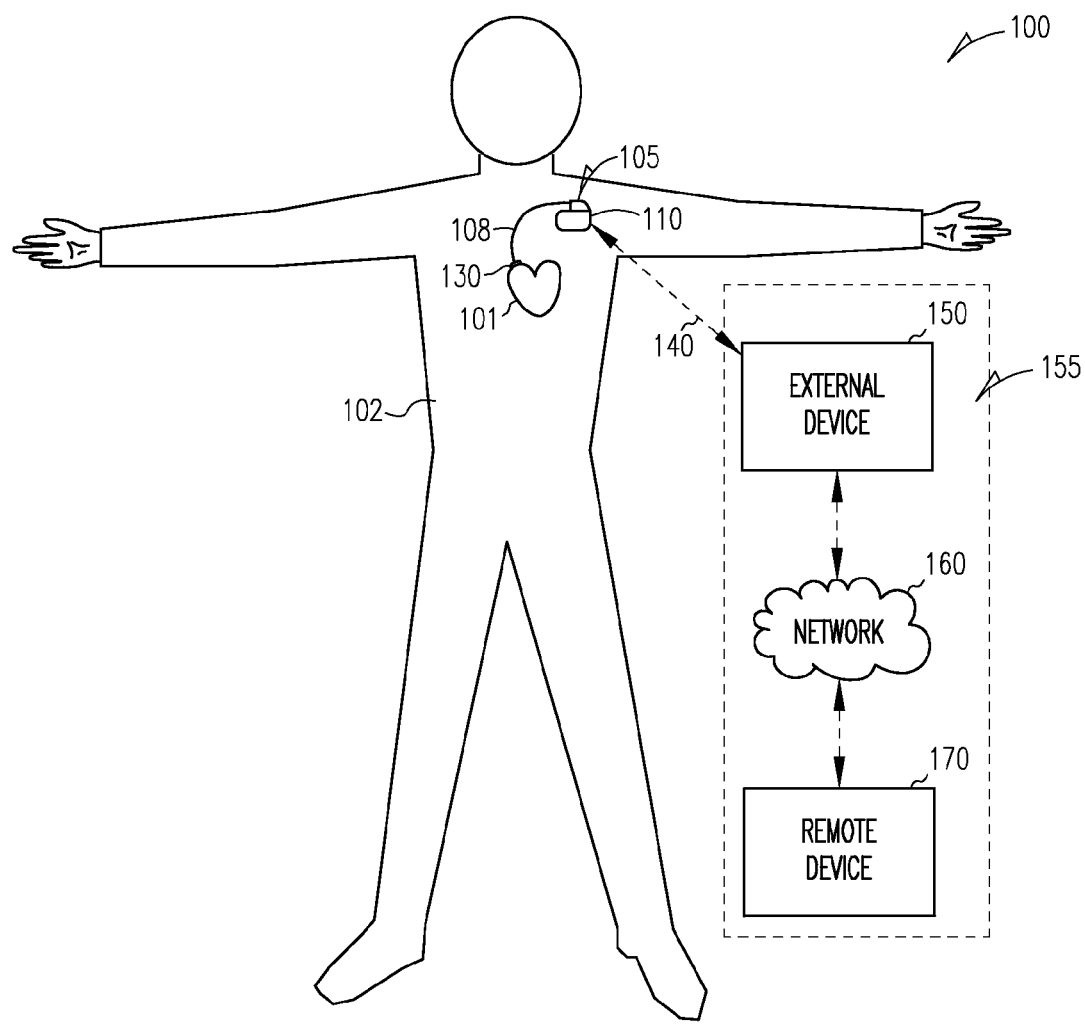
FIG. 1 is an illustration of an embodiment of a gene regulatory system including an implantable system and an external system and portions of an environment in which the gene regulatory system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses an implantable system for controlling a biologic therapy, e.g., a cardiac protection biologic therapy. Cardiac protection therapies such as ischemic postconditioning, ischemic preconditioning, pacing postconditioning, and pacing preconditioning have shown positive effects in reducing or minimizing myocardial tissue damage caused by ischemic events, including MI. Ischemic postconditioning protects the myocardium by inducing brief periods of ischemia after an ischemic event is detected. Ischemic preconditioning is a prophylactic therapy that protects the myocardium from an anticipated or predicted ischemic event by inducing brief periods of ischemia before the occurrence of the ischemic event. Pacing postconditioning protects the myocardium by delivering brief periods of a pacing therapy after an ischemic event is detected. Pacing preconditioning is a prophylactic therapy that protects the myocardium from an anticipated or predicted ischemic event by brief periods of a pacing therapy before the occurrence of such ischemic event. One specific example of pacing preconditioning is to deliver brief periods of pacing therapy to protect the myocardium from potentially recurring ischemic events after the pacing postconditioning has been delivered. Such pacing therapies change the distribution of stress in the myocardium, causing myocardial tissue to be stretched. Stretching of myocardial tissue may promote gene expression of therapeutic proteins that protect the myocardium from ongoing or subsequent ischemic damage. For example, mechanoreceptors in the myocardium may mediate the release of cardiac protective agents (i.e., secreted factor). According to one embodiment, an expression cassette encoding a desirable gene product is administered, e.g., injected, into myocardial tissue. The gene product, for example, activates the mechanoreceptors in the myocardium. The expression of the gene product is under the control of a transcriptional control element, such as a promoter, that can be regulated by a signal. An implantable system controls the expression of the gene product by delivering at least one gene regulatory signal that increases (or decreases) expression from the transcriptional control element. Thus, in one embodiment, in response to the gene regulatory signal, expression from the expression cassette results in synthesis of one or more therapeutic gene products that protect the myocardium from ischemic damage.

In one embodiment, the implantable system detects ischemic events. In response to the detection of an ischemic event, a cardiac protection biologic therapy is administered by delivering one or more gene regulatory signals after detection of the ischemic event (a postconditioning cardiac biologic therapy) and optionally, at a later time, delivering one or more gene regulatory signals (one or more prophylactic, i.e., preconditioning, cardiac biologic therapies). A postconditioning cardiac biologic therapy is delivered to protect the myocardium against damage caused by the detected ischemic event, while the one or more preconditioning cardiac biologic therapies are delivered to protect the myocardium against damage caused by recurrent ischemic events that may follow the detected ischemic event. The postconditioning cardiac biologic therapy and the one or more preconditioning cardiac biologic therapies may include delivery of one or more gene regulatory signals including alternating signaling and non-signaling periods. The signaling periods each have a defined duration during which at least one gene regulatory signal, of constant or varying strength (amplitude), is delivered. In other words, the postconditioning cardiac biologic therapy and the one or more preconditioning cardiac biologic therapies include intermittent transmission of the gene regulatory signal with a non-signaling period(s) each for a predetermined duration.

While an implantable system delivering a gene regulation therapy is specifically discussed in this document for illustrative purposes, the present subject matter is not limited to implantable systems. For example, the gene regulation therapy is also deliverable using a percutaneous lead or catheter connected to an external therapy controller or delivery device.

Definitions

"Cardiac protection biologic therapy" refers to the altered expression of one or more gene products that is controlled by a device, which one or more gene products directly or indirectly prevent, inhibit or treat damage or dysfunction of cardiac tissue resulting from decreased blood flow to the heart, and includes two or more sequential events of a defined duration. The first event generally includes a period of time of increased expression of a gene product encoded by a gene therapy vector, where the expression is increased due to a signal delivered from an implantable device, and the second event generally includes at least one period of time where expression of the gene product is reduced or eliminated, due to termination of the signal.

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamyvirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors is known in the art and is generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA*, 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

The term "transduction" denotes the delivery of a polynucleotide to a recipient cell either in vivo or in vitro, via a viral vector and preferably via a replication-defective viral vector, such as via a recombinant AAV.

The term "heterologous" as it relates to nucleic acid sequences such as gene sequences and control sequences, denotes sequences that are not normally joined together, and/ or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

By "cardiac-specific enhancer or promoter" is meant an element, which, when operably linked to a promoter or alone, respectively, directs gene expression in a cardiac cell and does not direct gene expression in all tissues or all cell types. Cardiac-specific enhancers or promoters may be naturally occurring or non-naturally occurring. One skilled in the art will recognize that the synthesis of non-naturally occurring enhancers or promoters can be performed using standard oligonucleotide synthesis techniques.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a signal or targeting peptide sequence is operably linked to another protein if the resulting fusion is secreted from a cell as a result of the presence of a secretory signal peptide or into an organelle as a result of the presence of an organelle targeting peptide.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide, virus or other biological component with which it is ordinarily associated in its natural source. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

By "growth factor" is meant an agent that, at least, promotes cell growth or induces phenotypic changes.

The term "angiogenic" means an agent that alone or in combination with other agents induces angiogenesis, and includes, but is not limited to, fibroblast growth factor (FGF), basic FGF, vascular endothelial growth factor (VEGF), hepatocyte growth factor, angiogenin, transforming growth factor (TGF), tissue necrosis factor (TNF, e.g., TNF-α), platelet derived growth factor (PDGF), granulocyte colony stimulatory factor (GCSF), placental GF, IL-8, proliferin, angiopoietin, e.g., angiopoietin-1 and angiopoietin-2, thrombospondin, ephrin-A1, E-selectin, leptin and heparin affinity regulatory peptide.

"Gene regulation" or "Gene regulatory therapy" as used herein includes delivery of one or more gene regulatory signals to regulate gene expression in a gene therapy vector. The gene regulatory signals include signals that trigger a transcriptional control element, e.g., a promoter.

A "user" includes a physician or other caregiver using a gene regulatory system to treat a patient.

Gene Regulatory System

FIG. 1 is an illustration of an embodiment of a gene regulatory system 100 and portions of an environment in which system 100 is used. System 100 includes an implantable system 105, an external system 155, and a telemetry link 140 providing for communication between implantable system 105 and external system 155.

Implantable system 105 includes, among other things, an implantable CRM device 110, a lead system 108, and an implantable gene regulatory signal delivery device 130. As shown in FIG. 1, implantable CRM device 110 is implanted in a body 102. Implantable CRM device 110 is an implantable medical device that detects ischemic events and may initiate one or more cardiac protective biologic therapies in response to the detection of each ischemic event. Implantable gene regulatory signal delivery device 130 delivers the one or more cardiac protection biologic therapies by emitting one or more gene regulatory signals to a heart 101, the vascular system of body 102, or any other site within body 102 targeted for the one or more cardiac protection biologic therapies. Lead system 108 provides for access to one or more locations to which the one or more gene regulatory signals are delivered. In one embodiment, lead system 108 includes one or more leads providing for electrical connections between implantable CRM device 110 and implantable gene regulatory signal delivery device 130. In another embodiment, lead system 108 provides for the transmission of the one or more gene regulatory signals to the locations to which the signals are delivered. In various embodiments, implantable CRM device 110 is an implantable medical device that also includes a pacemaker, a cardioverter/defibrillator, a cardiac resynchronization therapy (CRT) device, a cardiac remodeling control therapy (RCT) device, a drug delivery device or a drug delivery controller, a cell therapy device, any combination of these devices, or any other implantable medical device. Lead system 108 further includes leads for sensing physiological signals and delivering pacing pulses, cardioversion/defibrillation shocks, and/or pharmaceutical or other substances.

External system 155 receives information acquired using implantable CRM device 110 and allows a user such as a physician or other caregiver to control the operation of implantable system 105. In one embodiment, external system 155 includes a programmer. In another embodiment, as illustrated in FIG. 1, external system 155 includes a patient monitoring system that includes an external device 150, a network 160, and a remote device 170. External device 150 is within the vicinity of implantable CRM device 110 and communicates with implantable CRM device 110 bi-directionally via telemetry link 140. Remote device 170 is in a remote location and communicates with external device 150 bi-directionally via network 160, thus allowing a user to monitor and treat a patient from a distant location.

System 100 allows the delivery of a cardiac protection biologic therapy via emission of the one or more gene regulatory signals, to be triggered by any one of implantable CRM device 110, an implantable sensor or other component coupled to implantable CRM device 110, external device 150, and remote device 170. In one embodiment, implantable CRM device 110 triggers the delivery of cardiac protection biologic therapy upon detecting a predetermined parameter or condition, such as the occurrence of an ischemic event. In another embodiment, external device 150 or remote device 170 triggers the delivery of cardiac protection biologic therapy upon detecting an abnormal condition from a signal transmitted from implantable CRM device 110. In a specific embodiment, external system 155 includes a processor running a therapy decision algorithm to determine whether and when to trigger the delivery of the cardiac protection biologic therapy. In another specific embodiment, external system 155 includes a user interface to present signals acquired by implantable CRM device 155 and/or a detected abnormal condition or parameter to a user and receives commands from the user for triggering the delivery of the gene therapy. In another specific embodiment, the user interface includes a user input incorporated into external device 150 to receive commands from the user and/or the patient treated with system 100. For example, the patient may be instructed to enter a command for the cardiac protection biologic therapy when he senses certain symptoms, and another person near the patient may do the same upon observing the symptoms.

Figure 2:
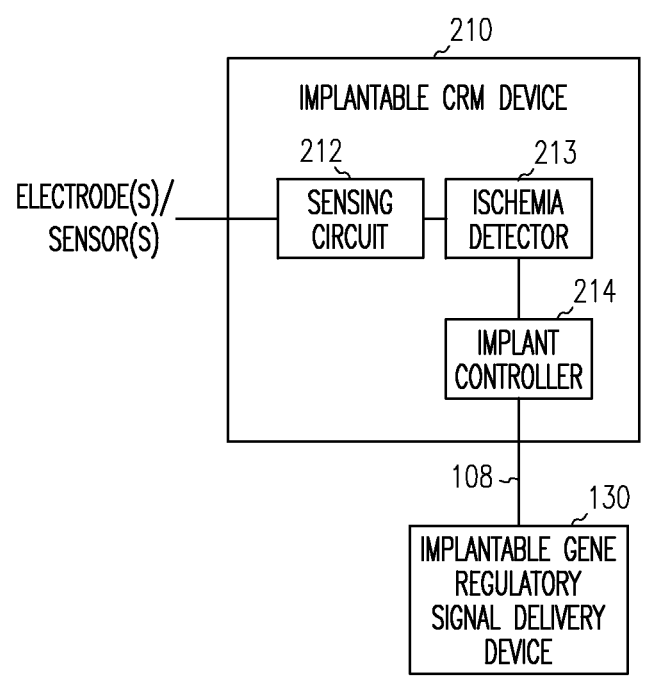
FIG. 2 is a block diagram illustrating an embodiment of portions of a circuit of the implantable system.

FIG. 2 is a block diagram showing one embodiment of the circuit of portions of system 100 including an implantable CRM device 210, lead system 108, and implantable gene regulatory signal delivery device 130. Implantable CRM device 210 represents a specific embodiment of implantable CRM device 110. In one embodiment, lead system 108 provides for an electrical connection between implantable CRM device 210 and implantable gene regulatory signal delivery device 130, such that implantable CRM device 210 transmits a voltage or current signal to control the delivery of a gene regulatory signal.

Implantable gene regulatory signal delivery device 130 receives a gene regulatory control signal from implantable CRM device 210 and, in response, delivers one or more gene regulatory signals in one or more forms of energy so as to regulate gene expression in a gene therapy vector. The forms of energy include electrical energy, electromagnetic energy, optical energy, acoustic energy, thermal energy, and any other form of energy that regulates expression in a gene therapy vector. In various embodiments, the one or more gene regulatory signals are each capable of regulating gene expression without inducing cardiac depolarization. For example, the one or more gene regulatory signals are each in a form of energy that is not known to excite myocardial tissue to cause depolarization of a cardiac chamber or in a level of intensity that does not excite myocardial tissue to cause depolarization of a cardiac chamber. In one embodiment, implantable gene regulatory signal delivery device 130 delivers one or more gene regulatory signals to the heart. In a specific embodiment, implantable gene regulatory signal delivery device 130 is an implantable device designed for placement in or on the heart. In another embodiment, implantable gene regulatory signal delivery device 130 delivers the one or more gene regulatory signals to the blood. In a specific embodiment, implantable gene regulatory signal delivery device 130 is an implantable device designed for placement within the vascular system, such as in a vein.

In one embodiment, implantable gene regulatory signal delivery device 130 includes an electric field generator that generates and emits an electric field. The electric field has frequency and strength parameters selected for regulating gene expression in an exogenously introduced vector. In one specific embodiment, an electric field generator includes electrodes to which a voltage is applied. The intensity of the electric field is controlled by controlling the voltage across the electrodes.

In one embodiment, implantable gene regulatory signal delivery device 130 includes an electromagnetic field generator that generates and emits an electromagnetic field. The electromagnetic field has frequency and strength parameters selected for regulating gene expression in an exogenously introduced vector. In one specific embodiment, the electromagnetic field generator includes an inductive coil. The intensity of the electromagnetic field is controlled by controlling the voltage across the coil and/or the current flowing through it. In one specific embodiment, the electromagnetic field has a frequency of about 1 Hz to 1 kHz. In another specific embodiment, the electromagnetic field is a direct-current (dc) electromagnetic field.

In one embodiment, implantable gene regulatory signal delivery device 130 includes an optical emitter that emits light. The light has wavelength and intensity parameters selected for regulating gene expression. In one specific embodiment, the optical emitter includes a light-emitting diode (LED). The intensity of the light is controlled by controlling the voltage across the LED and/or the current flowing through it. In another specific embodiment, the optical emitter includes an array of LEDs that can be programmed to emit lights having one or more distinct wavelengths.

In one embodiment, implantable gene regulatory signal delivery device 130 includes an acoustic emitter that emits an acoustic signal such as a sound or an ultrasound signal. The sound has frequency and intensity parameters selected for regulating gene expression in an exogenously introduced vector.

In one embodiment, implantable gene regulatory signal delivery device 130 includes a drug delivery device which emits one or more chemical agents. The one or more chemical agents have properties known to regulate expression from a transcriptional control element. Examples of the one or more chemical agents include chemicals which induce expression from a particular promoter, including tetracycline, rapamycin, auxins, metals, and ecdysone.

In one embodiment, implantable gene regulatory signal delivery device 130 includes a thermal radiator that emits a thermal energy. The thermal energy changes the tissue temperature to a point or range suitable for regulating gene expression in an exogenously introduced vector. In one specific embodiment, the thermal radiator includes a resistive element that is heated when an electrical current flows through it or as a voltage is applied across it. The tissue temperature is controlled by controlling the amplitude of the electrical current or voltage.

Implantable CRM device 210 includes a sensing circuit 212, an ischemia detector 213, and an implant controller 214. Implantable CRM device 210 includes a hermetically sealed metal can to house at least portion of the electronics of the device.

Sensing circuit 212 senses the one or more physiological parameters, or changes in one or more of the parameters, indicative of an ischemic event(s) through one or more electrodes and/or sensors. In various embodiments, the electrode(s) include one or more electrodes incorporated into a lead of lead system 108, one or more electrodes incorporated onto implantable CRM device 210, and/or the metal can functioning as an electrode. In various embodiments, the sensor(s) includes one or more sensors incorporated into a lead of lead system 108, one or more sensors incorporated into implantable gene regulatory signal delivery device 130, one or more sensors incorporated onto implantable CRM device 210, one or more sensors housed within implantable CRM device 210, one or more sensors as separate implantable devices communicating with implantable CRM device 210, and/or one or more external (non-implantable) sensors communicating with implantable CRM device 210.

Ischemia detector 213 detects the ischemic events from the one or more physiological parameters, or change(s) in one or more of the parameters, indicative of an ischemic event(s). Implant controller 214 is a microprocessor-based control circuit that controls the delivery of the one or more gene regulatory signals in response to the detection of at least one ischemic event and/or using the one or more parameters sensed by sensing circuit 212. In various embodiments, ischemia detector 213 and implant controller 214 are each implemented as portions of a microprocessor-based system.

Ischemia detector 213 includes an ischemia analyzer running an automatic ischemia detection algorithm to detect the ischemic event from the one or more physiological parameters or changes therein. In one embodiment, ischemia detector 213 produces an ischemia alert signal indicative of the detection of each ischemic event. In one embodiment, in response to the ischemia alert signal, implantable CRM device 210 produces an alarm signal, such as a predetermined audio tone, that is perceivable by the patient. In another embodiment, the ischemia signal is transmitted to external system 155 for producing an alarm signal and/or a warning message for the user and/or the patient.

In one embodiment, ischemia detector 213 detects the ischemic events from one or more cardiac parameters or changes therein. Sensing circuit 212 includes a cardiac sensing circuit. In a specific example, cardiac parameters are sensed using a wearable vest including embedded electrodes configured to sense surface biopotential parameters indicative of cardiac activities. The sensed surface biopotential parameters are transmitted to implantable CRM device 110 via telemetry. In another specific embodiment, ischemia detector 213 detects the ischemic events from one or more wireless electrocardiograms (ECG). Sensing circuit 212 includes a wireless ECG sensing circuit. A wireless ECG approximates the surface ECG and is acquired without using surface (skin contact) electrodes. An example of a circuit for sensing the wireless ECG is discussed in U.S. Pat. No. 7,299,086 entitled "WIRELESS ECG IN IMPLANTABLE DEVICES," filed on Mar. 5, 2004, assigned to Cardiac Pacemakers, Inc., which is incorporated by reference in its entirety. An example of a wireless ECG-based ischemia detector is discussed in U.S. patent application Ser. No. 11/079,744, entitled "CARDIAC ACTIVATION SEQUENCE MONITORING FOR ISCHEMIA DETECTION," filed on Mar. 14, 2005, assigned to Cardiac Pacemakers, Inc., which is incorporated by reference in its entirety. In another embodiment, ischemia detector 213 detects the ischemic events from one or more electrograms. Sensing circuit 212 includes an electrogram sensing circuit. Examples of an electrogram-based ischemia detector are discussed in U.S. Pat. No. 6,108,577, entitled, "METHOD AND APPARATUS FOR DETECTING CHANGES IN ELECTROCARDIOGRAM SIGNALS," and U.S. Pat. No. 7,340,303, entitled "EVOKED RESPONSE SENSING FOR ISCHEMIA DETECTION," filed on Sep. 25, 2001, both assigned to Cardiac Pacemakers, Inc., which are incorporated herein by reference in their entirety.

In another embodiment, ischemia detector 213 detects the ischemic events from one or more impedance parameters. Sensing circuit 212 includes an impedance sensing circuit to sense one or more impedance parameters each indicative of a cardiac impedance or a transthoracic impedance. Ischemia detector 213 includes an electrical impedance based sensor using a low carrier frequency to detect the ischemic events from electrical impedance. Tissue electrical impedance has been shown to increase significantly during ischemia and decrease significantly after ischemia, as discussed in Dzwonczyk, et al. *IEEE Trans. Biomed. Eng.,* 51(12): 2206-09 (2004). The ischemia detector senses low frequency electrical impedance between electrodes interposed in the heart, and detects the ischemia as abrupt changes in impedance (such as abrupt increases in value). In a specific embodiment, ischemia detector 213 monitors complex impedance with concentration on the reactance to detect the ischemic events. Because ischemia induced changes in impedance occur predominantly in the reactive component, concentrating on the reactive component of the impedance provides for a high sensitivity of ischemia detection. In another specific embodiment, ischemia detector 213 detects the ischemic events from multiple impedance parameters sensed through multiple electrodes positioned to monitor ventricular regional volumes or wall motion. The impedance parameters are indicative of changes in regional cardiac contractions resulting from ischemia. The ischemic events are detected by analyzing morphological and/or timing changes in the impedance parameters, such as by using a template matching technique.

In another embodiment, ischemia detector 213 detects the ischemic events from one or more parameters indicative of heart sounds. Sensing circuit 212 includes a heart sound sensing circuit. The heart sound sensing circuit senses the one or more parameters indicative of heart sounds using one or more sensors such as accelerometers and/or microphones. Such sensors are included in implantable CRM device 110 or incorporated into lead system 108. Ischemia detector 213 detects the ischemic event by detecting predetermined type heart sounds, predetermined type heart sound components, predetermined type morphological characteristics of heart sounds, or other characteristics of heart sounds indicative of ischemia.

In another embodiment, ischemia detector 213 detects the ischemic events from one or more pressure parameters. Sensing circuit 212 includes a pressure sensing circuit coupled to one or more pressure sensors. In a specific embodiment, the pressure sensor is an implantable pressure sensor sensing a parameter indicative of an intracardiac or intravascular pressure whose characteristics are indicative of ischemia.

In another embodiment, ischemia detector 213 detects the ischemic event from one or more acceleration parameters each indicative of regional cardiac wall motion. Sensing circuit 212 includes a cardiac motion sensing circuit coupled to one or more accelerometers each incorporated into a portion of a lead positioned on or in the heart. The ischemia detector detects ischemia as an abrupt decrease in the amplitude of local cardiac accelerations.

In another embodiment, ischemia detector 213 detects the ischemic event from a parameter indicative of heart rate variability (HRV). Sensing circuit 212 includes an HRV sensing circuit to sense and produce a parameter which is representative of a HRV. HRV is the beat-to-beat variance in cardiac cycle length over a period of time. The HRV parameter includes any parameter being a measure of the HRV, including any qualitative expression of the beat-to-beat variance in cardiac cycle length over a period of time. In a specific embodiment, the HRV parameter includes the ratio of Low-Frequency (LF) HRV to High-Frequency (HF) HRV (LF/HF ratio). The LF HRV includes components of the HRV having frequencies between about 0.04 Hz and 0.15 Hz. The HF HRV includes components of the HRV having frequencies between about 0.15 Hz and 0.40 Hz. The ischemia detector detects ischemia when the LF/HF ratio exceeds a predetermined threshold. An example of an LF/HF ratio-based ischemia detector is discussed in U.S. patent application Ser. No. 7,215,992, entitled "METHOD FOR ISCHEMIA DETECTION BY IMPLANTABLE CARDIAC DEVICE," filed on Sep. 23, 2003, assigned to Cardiac Pacemakers, Inc., which is incorporated by reference in its entirety.

Figure 3:
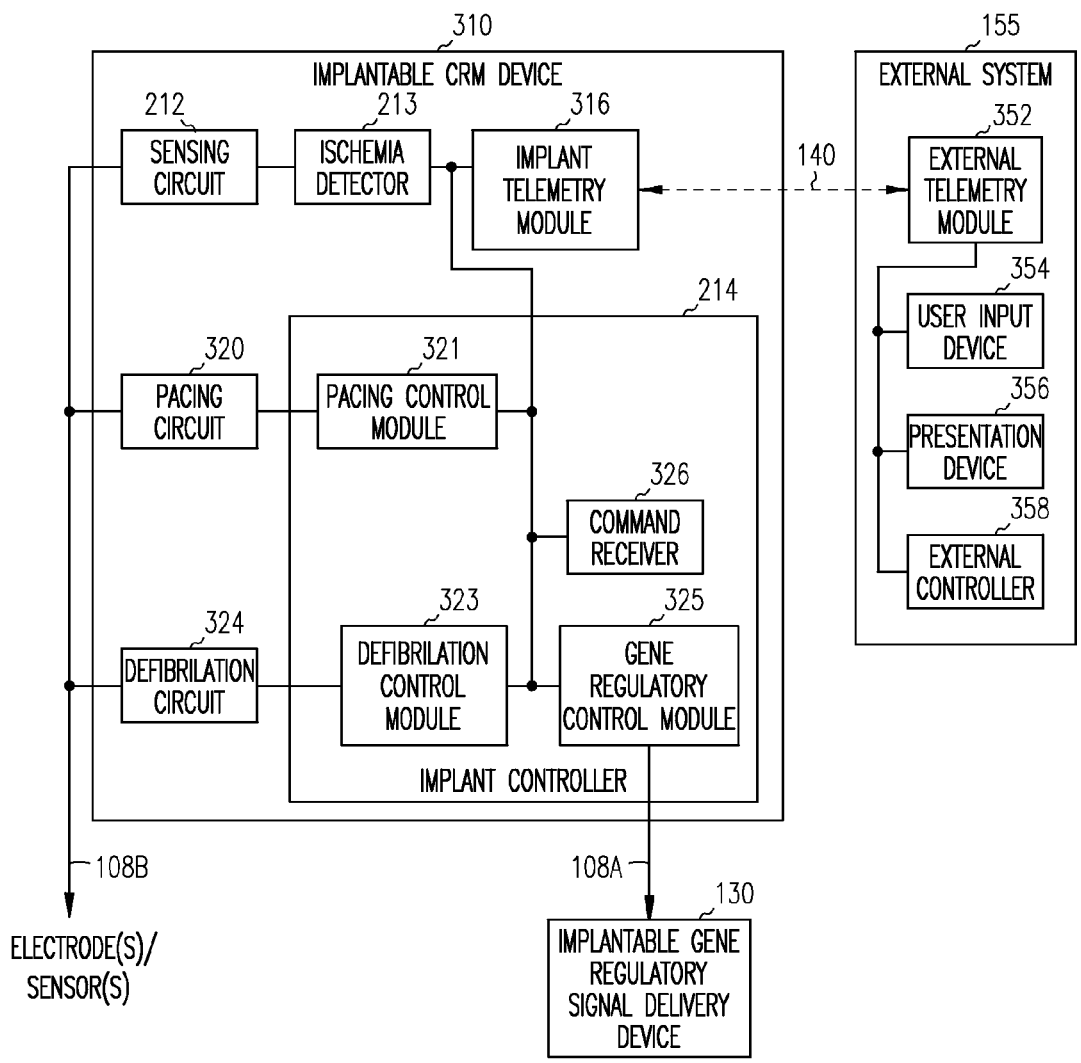
FIG. 3 is a block diagram illustrating a specific embodiment of portions of the circuit of the implantable system.

FIG. 3 is a block diagram showing another embodiment of the circuit of portions of system 100 including an implantable CRM device 310, lead system 108, implantable gene regulatory signal delivery device 130, and external system 155. Implantable CRM device 310 represents a specific embodiment of implantable CRM device 210 and includes pacing and defibrillation capabilities. In addition to controlling cardiac protection biologic therapies, implantable CRM device 310 delivers therapies including, but not limited to, one or more of bradyarrhythmia pacing, anti-tachyarrhythmia pacing, atrial and/or ventricular cardioversion/defibrillation, CRT, RCT, and drug delivery. However, such therapeutic capabilities are not necessary for system 100 to control gene therapy, and hence, are not necessary elements of implantable CRM device 310. In other words, implantable CRM device 310 can be an implantable pacemaker and/or defibrillator with additional functions including control of gene therapy, or it can be a dedicated implantable gene therapy controller.

In the embodiment illustrated in FIG. 3, implantable CRM device 310 includes sensing circuit 212, ischemia detector 213, implant controller 214, a pacing circuit 320, a defibrillation circuit 324, and an implant telemetry module 316. Pacing circuit 320 delivers pacing pulses to one or more cardiac regions as controlled by implant controller 214. Defibrillation circuit 324 delivers cardioversion/defibrillation shocks to one or more cardiac regions as controlled by implant controller 214. Implant controller 214 includes a gene regulation control module 325, a pacing control module 321, a defibrillation control module 323, and a command receiver 326. Gene regulation control module 325 generates the gene regulatory signal in response to an ischemia event detected by ischemia detector 213 or in response to a gene regulatory command received by command receiver 326. Command receiver 326 receives the gene regulatory command from external system 155 via telemetry link 140. Pacing control module 321 controls the delivery of pacing pulses from pacing circuit 320 according to a bradyarrhythmia pacing algorithm, a CRT algorithm, and/or an RCT algorithm. Defibrillation control module 323 controls the delivery of cardioversion/defibrillation shocks from defibrillation circuit 324 when a tachyarrhythmic condition is detected. In one embodiment, defibrillation control module 323 includes an atrial defibrillation control module to control the delivery of cardioversion/defibrillation shocks to one or more of the atria. In one embodiment, defibrillation control module 323 includes a ventricular defibrillation control module to control the delivery of cardioversion/defibrillation shocks to one or more of the ventricles.

Lead system 108 includes one or more leads connecting implantable CRM device 310 and implantable gene regulatory signal delivery device 130, referenced as lead system 108A, and pacing leads, defibrillation leads, pacing-defibrillation leads, or any combination of such leads, referenced as lead system 108B. Lead system 108B allows sensing of electrical parameters from various regions of heart 101 and/or delivery of pacing pulses and/or defibrillation shocks to various regions of heart 101. The various regions of heart 101 includes regions within or about the right atrium (RA), left atrium (LA), right ventricle (RV), and left ventricle (LV). In one embodiment, lead system 108B includes one or more transvenous leads each having at least one sensing-pacing or defibrillation electrode disposed within heart 101. In one embodiment, lead system 108B includes one or more epicardial leads each having at least one sensing-pacing or defibrillation electrode disposed on heart 101. In one embodiment, lead system 108B includes at least one atrial defibrillation electrode disposed in or about one or both of the atria to allow atrial defibrillation. In one embodiment, lead system 108B includes at least one ventricular defibrillation electrode disposed in or about one or both of the ventricles to allow ventricular defibrillation.

External system 155 includes an external telemetry module 352, an external user input device 354, a representation device 356, and an external controller 358. In the embodiment in which external system 155 includes a patient management system, these system components distribute in one or more of external device 150, network 160, and remote device 170, depending on design and medical considerations. User input device 354 receives commands from the user and/or the patient to control the delivery of the cardiac protection biologic therapy, i.e., the delivery of the one or more gene regulatory signals. Presentation device 356 displays or otherwise presents parameters acquired and/or information regarding events detected by implantable CRM device 310. External controller 358 controls the operation of external system 155. In one embodiment, external controller 358 includes an ischemia alert signal receiver that receives the ischemia alert signal produced by ischemia detector 213 and transmitted via telemetry link 140. Presentation device 356 presents an alarm signal and/or a warning message in response to the ischemia alert signal. In a specific embodiment, presentation device 356 includes a speaker to produce an audible alarm signal and/or an audible warning message in response to the ischemia alert signal. The audible alarm signal and/or warning message call for immediate attention of the patient or a physician or other caregiver. In a further specific embodiment, presentation device 356 also includes a display to visually display the alarm signal and/or warning message. In one embodiment, external controller 358 further provides automatic control of operations of implantable CRM device 310. In one embodiment, user input device 352 receives the gene regulatory command entered by the user based on observations of the parameters and/or abnormal conditions presented by presentation device 356. In another embodiment, user input device 352 receives the gene regulatory command entered by the patient when the patient physically senses a symptom indicative of an immediate need for the gene regulatory therapy, or entered by a person near the patient who observes a symptom indicative of the immediate need for the cardiac protection biologic therapy. In a further embodiment, external controller 358 automatically analyzes the signals acquired and/or events detected by implantable CRM device 310 and generates the gene regulatory command when deemed necessary based on the result of the analysis.

Telemetry link 140 is a wireless bidirectional data transmission link supported by implant telemetry module 316 and external telemetry module 352. In one embodiment, telemetry link 140 is an inductive couple formed when two coils— one connected to implant telemetry module 316 and the other connected to external telemetry module 352—are placed near each other. In another embodiment, telemetry link 140 is a far-field radio-frequency telemetry link allowing implantable CRM device 310 and external system 155 to communicate over a telemetry range that is at least ten feet.

Figure 4:
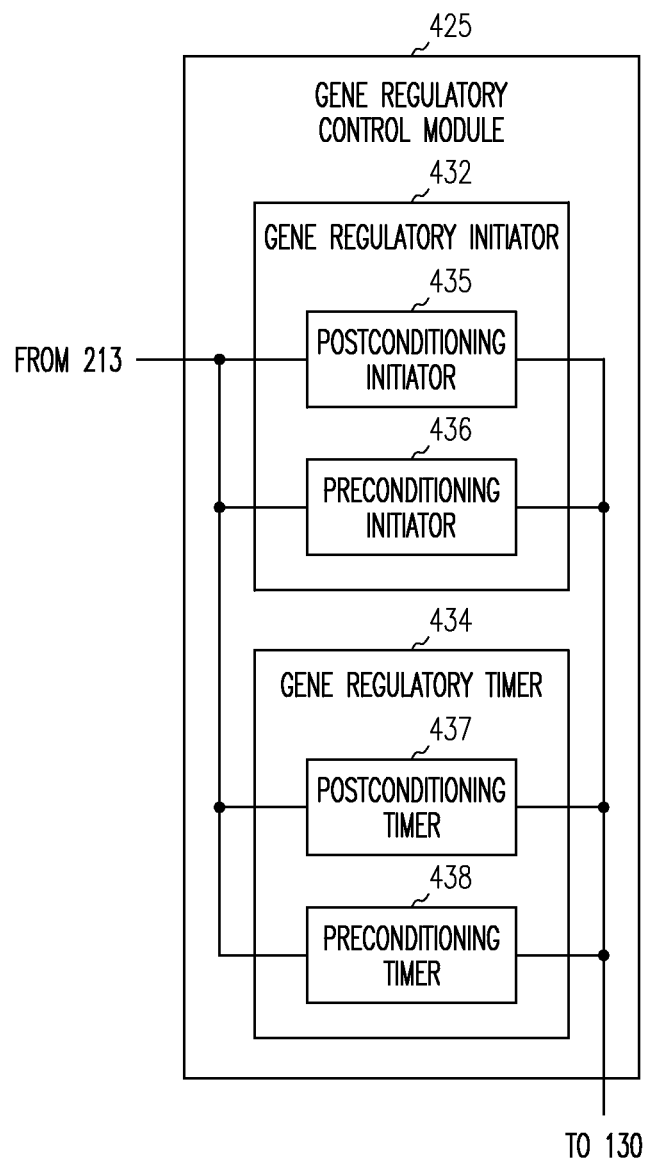
FIG. 4 is a block diagram illustrating an embodiment of a gene regulatory control module of the implantable system.
Figure 7:
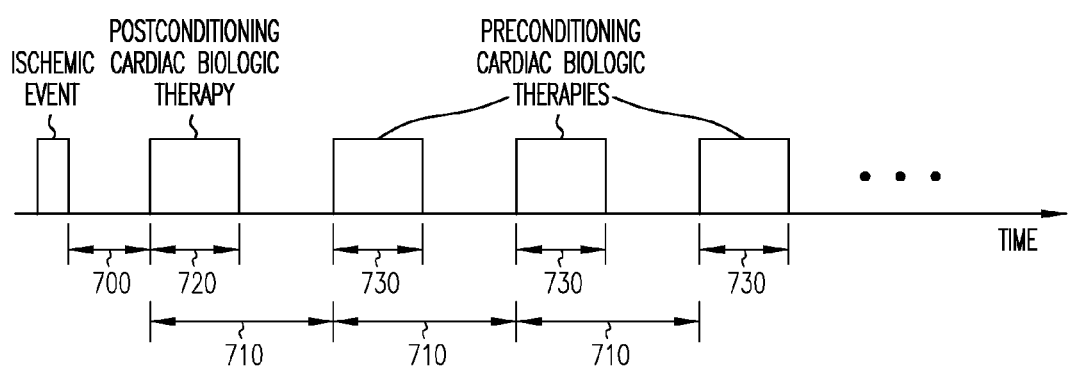
FIG. 7 is an illustration of an embodiment of timing of cardiac protection biologic therapies delivered after an ischemic event.
Figure 8:
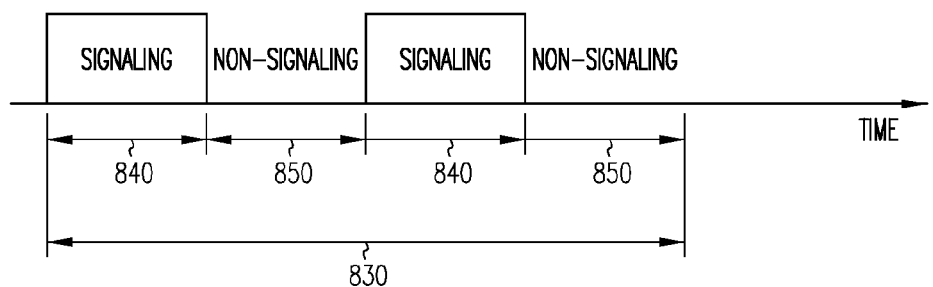
FIG. 8 is an illustration of an embodiment of timing of gene regulatory signaling and non-signaling periods of a cardiac protection biologic therapy.

FIG. 4 is a block diagram illustrating an embodiment of a gene regulatory control module 425, which is a specific embodiment of gene regulatory control module 325. Gene regulatory control module 425 includes a gene regulatory initiator 432 and a gene regulatory timer 434. Various timing intervals controlled by gene regulatory control module 425 are illustrated in FIGS. 7 and 8.

Gene regulatory initiator 432 initiates one or more cardiac protection biologic therapies in response to the detection of an ischemic event. In one embodiment, gene regulatory initiator 432 also initiates one or more cardiac protection biologic therapies in response to each gene regulatory command received by external system 155. For example, following a diagnosis of vulnerable plaque indicative of a high risk for MI, a physician applies a preconditioning cardiac biologic therapy by issuing a gene regulatory command to start a cardiac protection biologic therapy. Gene regulatory timer 434 times each gene regulatory signaling period and non-signaling period.

In one embodiment, in response to the detection of each ischemic event, gene regulatory initiator 432 initiates a post-conditioning cardiac biologic therapy with at least one period for signal emission and optionally including a particular signal strength, and another period for no signal emission. In a further embodiment, following the delivery of the postconditioning cardiac biologic therapy, gene regulatory initiator 432 initiates a plurality of preconditioning cardiac biologic therapies with individual periods for each signal emission, and optionally including a particular signal strength, and individual periods for no signal emission. In one embodiment, in response to the detection of another ischemic event, gene regulatory initiator 432 terminates any ongoing response to the detection of the previous ischemic event and initiates a new postconditioning cardiac biologic therapy, optionally followed by a new plurality of preconditioning cardiac biologic therapies. As illustrated in FIG. 4, gene regulatory initiator 432 includes a postconditioning initiator 435 and a preconditioning initiator 436, and gene regulatory timer 434 includes a postconditioning timer 437 and a preconditioning timer 438.

Postconditioning initiator 435 initiates the postconditioning cardiac biologic therapy in response to the detection of an ischemic event. In one embodiment, postconditioning initiator 435 initiates the postconditioning cardiac biologic therapy when the end of the ischemic event is detected. In one embodiment, the end of the ischemic event is detected when the ischemic event is no longer detected by ischemia detector 213. In one embodiment, postconditioning initiator 435 initiates the postconditioning cardiac biologic therapy when a post-ischemia time interval expires. The post-ischemia time interval starts when the end of the ischemic event is detected and is up to approximately 10 minutes, with approximately 30 seconds being a specific example. In one embodiment, the post-ischemia time interval is chosen such that the postconditioning cardiac biologic therapy is initiated after the reperfusion phase following the ischemic event has started. In another embodiment, postconditioning initiator 435 initiates the postconditioning cardiac biologic therapy in response to one or more postconditioning commands transmitted from external system 155.

Preconditioning initiator 436 initiates the preconditioning cardiac biologic therapies, one at a time, after the end of the ischemic event is detected and the postconditioning cardiac biologic therapy is completed. In one embodiment, preconditioning initiator 436 initiates the preconditioning cardiac biologic therapies on a periodic basis using a predetermined period. The predetermined period is in a range of approximately 24 hours to 72 hours, with approximately 48 hours being a specific example. In another embodiment, preconditioning initiator 436 initiates the preconditioning cardiac biologic therapy according to a programmed preconditioning schedule. In another embodiment, preconditioning sequence initiator 436 initiates the preconditioning cardiac biologic therapy in response to one or more preconditioning commands transmitted from external system 155.

Postconditioning timer 437 times the postconditioning cardiac biologic therapy including alternating postconditioning signaling and non-signaling periods. Each postconditioning signaling period has a postconditioning signaling duration during which the one or more gene regulatory signals are emitted. Each postconditioning non-signaling period has a postconditioning non-signaling duration during which no gene regulatory signal is emitted. The postconditioning cardiac biologic therapy has a postconditioning therapy duration in a range of approximately 30 seconds to 1 hour, with approximately 10 minutes being a specific example. The postconditioning signaling duration is in a range of approximately 5 seconds to 10 minutes, with approximately 30 seconds as a specific example. The postconditioning non-signaling duration is in a range of approximately 5 seconds to 10 minutes, with approximately 30 seconds as a specific example.

Preconditioning timer 438 times the preconditioning cardiac biologic therapies each including alternating preconditioning signaling and non-signaling periods. The preconditioning signaling periods each have a preconditioning signaling duration during which the one or more gene regulatory signals are emitted. The preconditioning non-signaling periods each have a preconditioning non-signaling duration during which no gene regulatory signal is emitted. The preconditioning cardiac biologic therapies each have a preconditioning therapy duration in a range of approximately 2 minutes to 1 hour, with approximately 10 minutes being a specific example. The preconditioning signaling duration is in a range of approximately 1 minute to 30 minutes, with approximately 5 minutes being a specific example. The preconditioning non-signaling duration is in a range of approximately 1 minute to 30 minutes, with approximately 5 minutes being a specific example.

In one embodiment, gene regulatory control module 425 suspends the one or more regulatory signals in response to the detection of a predetermined type arrhythmia. In one embodiment, gene regulation signal initiator 432 cancels, holds, or otherwise adjusts the timing of the initiation of a regulatory signal in response to the detection of a predetermined type arrhythmia. In one embodiment, gene regulatory timer 434 terminates or suspends a regulatory signal in response to the detection of an arrhythmia that occurs during a cardiac protection biologic therapy. In a specific embodiment, postconditioning initiator 435 cancels the initiation of a postconditioning cardiac biologic therapy in response to the detection of arrhythmia. In a specific embodiment, preconditioning initiator 436 holds the initiation of a preconditioning cardiac biologic therapy in response to the detection of arrhythmia unit the arrhythmia is no longer detected.

Figure 5:
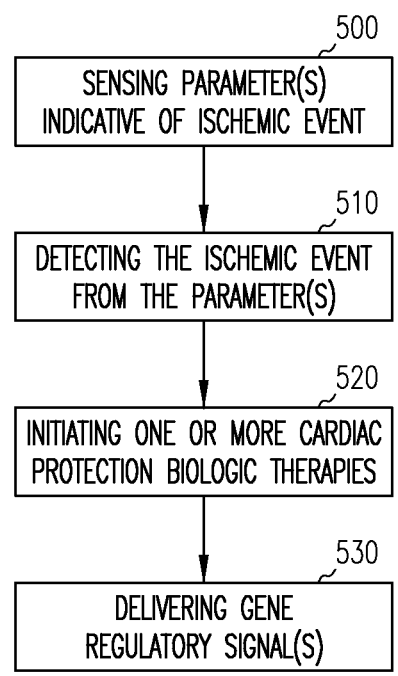
FIG. 5 is a flow chart illustrating an embodiment of a method for gene regulation for cardiac protection.

FIG. 5 is a flow chart illustrating an embodiment of a method for delivering a biologic therapy for cardiac protection against tissue damage associated with ischemic events. In one embodiment, the method is performed by system 100.

One or more parameters indicative of an ischemic event are sensed at 500. The ischemic event is detected from the one or more parameters at 510. In response to the detection of the ischemic event, one or more cardiac protection biologic therapies are initiated at 520. The one or more cardiac protection biologic therapies each include alternating signaling and non-signaling periods. The signaling periods each have a signaling duration during which one or more gene regulatory signals are delivered. The non-signaling periods each have a non-signaling duration during which no gene regulatory signal is delivered. The one or more gene regulatory signals are delivered during each of the signaling periods at 530. The delivery of the one or more gene regulatory signals includes emission of signals in one or more forms of energy being external factors regulating one or more gene expressions. The forms of energy include electrical energy, electromagnetic energy, optical energy, acoustic energy, thermal energy, and any other form of energy that triggers the gene regulatory system.

Figure 6:
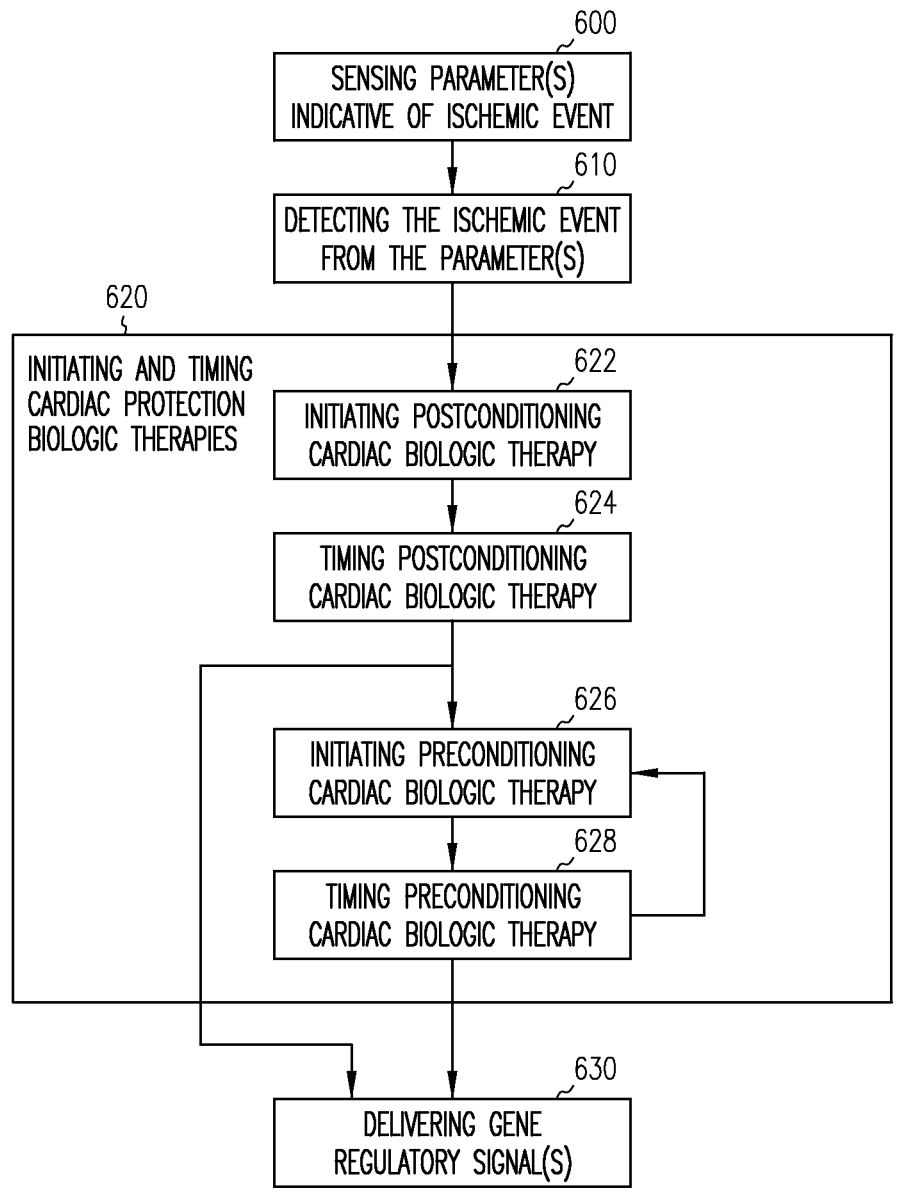
FIG. 6 is a flow chart illustrating a specific embodiment of the method for gene regulation for cardiac protection.

FIG. 6 is a flow chart illustrating a specific embodiment of the method for delivering the biologic therapy for cardiac protection that is discussed with reference to FIG. 5. In one embodiment, the method is performed by system 100.

One or more parameters indicative of an ischemic event are sensed at 600. The one or more parameters are selected from surface ECG or other surface biopotential parameters indicative of cardiac activities, wireless ECG, electrograms, impedance parameters, heart sound parameters, pressure parameters, acceleration parameters, parameters representative of HRV, and/or any other parameters having characteristics allowing detection of ischemic events.

The ischemic event is detected from the one or more parameters at 610, by running an automatic ischemia detection algorithm. In one embodiment, an ischemia alert signal is produced to indicate the detection of the ischemic event to the patient and/or a user such as a physician or other caregiver.

In response to the detection of the ischemic event, cardiac protection biologic therapy is initiated and timed at 620. In one embodiment, one or more cardiac protection biologic therapies are also initiated in response to gene regulatory commands issued by the user or the patient. The cardiac protection biologic therapies may include at least one postconditioning cardiac biologic therapy and a plurality of preconditioning cardiac biologic therapies. In response to the detection of the ischemic event, the postconditioning cardiac biologic therapy is initiated at 622. In one embodiment, the postconditioning cardiac biologic therapy is initiated when the end of the ischemic event is detected. In a specific embodiment, the end of the ischemic event is detected when the ischemic event is no longer detected. In a specific embodiment, the postconditioning cardiac biologic therapy is initiated when a post-ischemia time interval expires. The post-ischemia time interval starts at the end of the ischemic event and ends after a predicted reperfusion period following the ischemic event has started. In another embodiment, the postconditioning cardiac biologic therapy is initiated in response to a postconditioning command issued by a user. After being initiated, the postconditioning cardiac biologic therapy including alternating postconditioning signaling and non-signaling periods is timed at 624. The postconditioning signaling periods each have a postconditioning signaling duration during which at least one gene regulatory signal is delivered. The postconditioning non-signaling periods each have a postconditioning non-signaling duration during which no gene regulatory signal is delivered. After the postconditioning cardiac biologic therapy is completed, the preconditioning cardiac biologic therapies may be initiated, one at a time, at 626. In one embodiment, the preconditioning cardiac biologic therapies are initiated on a periodic basis with a predetermined period. In another embodiment, the preconditioning cardiac biologic therapies are initiated according to a preconditioning schedule programmed by the user. In another embodiment, the preconditioning cardiac biologic therapies are initiated in response to one or more preconditioning commands issued by the user. After being initiated, each of the preconditioning cardiac biologic therapies including alternating preconditioning signaling and non-signaling periods is timed at 628. The preconditioning signaling periods each have a preconditioning signaling duration during which at least one gene regulatory signal is delivered. The preconditioning non-signaling periods each have a preconditioning non-signaling duration during which no gene regulatory signal is delivered. In one embodiment, predetermined type arrhythmias are detected. The one or more cardiac protection biologic therapies are suspended in response to the detection of the arrhythmia.

The one or more gene regulatory signals are delivered during each of the signaling periods of the cardiac protection biologic therapies at 630. That includes the delivery of the gene regulatory signal during the postconditioning signaling periods of the postconditioning cardiac biologic therapy and the delivery of the gene regulatory signal during the preconditioning signaling periods of each of the preconditioning cardiac biologic therapies.

FIG. 7 is an illustration of an embodiment of timing of cardiac protection biologic therapies delivered after an ischemic event. A postconditioning cardiac biologic therapy is initiated in response to the detection of an ischemic event. A post-ischemia time interval 700 starts at the end of the ischemic event. Post-ischemia time interval 700 is up to approximately 10 minutes, with approximately 30 seconds being a specific example. When post-ischemia time interval 700 expires, the postconditioning cardiac biologic therapy is initiated. The postconditioning cardiac biologic therapy has a postconditioning therapy duration 720. Postconditioning therapy duration 720 is in a range of approximately 30 seconds to 1 hour, with approximately 10 minutes being a specific example. Then, preconditioning cardiac biologic therapies are initiated on a periodic basis each with an independent predetermined period 710. Predetermined period 710 is in a range of approximately 24 hours to 72 hours, with approximately 48 hours being a specific example. The preconditioning cardiac biologic therapies each have a preconditioning therapy duration 730. Preconditioning therapy duration 730 is in a range of approximately 2 minutes to 1 hour, with approximately 10 minutes being a specific example.

In one embodiment, if another ischemic event is detected after the postconditioning cardiac biologic therapy has been delivered, the timing of cardiac protection biologic therapies as illustrated in FIG. 7 restarts from the "ischemic event" point. In one embodiment, if no additional ischemic event is detected, the preconditioning cardiac biologic therapy are periodically delivered, as illustrated in FIG. 7, until it is terminated by a predetermined termination event, such as a command from a physician or other caregiver.

FIG. 8 is an illustration of an embodiment of timing of gene regulatory signaling and non-signaling periods of a cardiac protection biologic therapy. The cardiac protection biologic therapy has a therapy duration 830 and includes alternating signaling periods 840 and non-signaling periods 850. One or more gene regulatory signals are emitted during each of signaling periods 840. No gene regulatory signal is emitted during each of non-signaling periods 850.

Two pairs of alternating signaling period 840 and non-signaling period 850 are illustrated in FIG. 8 for illustrative but not restrictive purposes. In various embodiments, a cardiac protection biologic therapy may include one pair of signaling periods 840 and non-signaling periods 850, more than one pair of signaling periods 840 and non-signaling periods 850, or more than two pairs of signaling period 840 and non-signaling period 850.

In one embodiment, the cardiac protection biologic therapy is a postconditioning cardiac biologic therapy including alternating postconditioning signaling and non-signaling periods. Therapy duration 830 represents postconditioning therapy duration 720. Signaling periods 840 each represent a postconditioning signaling period having a postconditioning signaling duration in a range of approximately 5 seconds to 10 minutes, with approximately 30 seconds as a specific example. Non-signaling periods 850 each represent a postconditioning non-signaling period having a postconditioning non-signaling duration in a range of approximately 5 seconds to 10 minutes, with approximately 30 seconds as a specific example. In another embodiment, the cardiac protection biologic therapy is a preconditioning cardiac biologic therapy including alternating preconditioning signaling and non-signaling periods. Therapy duration 830 represents preconditioning therapy duration 730. Signaling periods 840 each represent a preconditioning signaling period having a preconditioning signaling duration is in a range of approximately 1 minute to 30 minutes, with approximately 5 minutes being a specific example. Non-signaling periods 850 each represent a preconditioning non-signaling period having a preconditioning non-signaling duration in a range of approximately 1 minute to 30 minutes, with approximately 5 minutes being a specific example.

The timing of the cardiac protection biologic therapies is illustrated in FIGS. 7 and 8 as an example, but not as a restriction. In one embodiment, gene regulatory control module 425 controls the illustrated timing of the cardiac protection biologic therapies.

Gene Therapy Vectors

Gene therapy vectors include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors is known in the art and is generally available.

Gene therapy vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene therapy vectors are described below. Gene therapy vectors may be administered via any route including, but not limited to, intramuscular, buccal, rectal, intravenous or intracoronary administration, and transfer to cells may be enhanced using electroporation and/or iontophoresis.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and non-dividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., Meth. Mol. Med., 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing cardiac specific promoters. In addition, adenoviral vectors can be produced at very high titers, allowing efficient gene transfer with small volumes of virus.

Adeno-associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., Nat. Med., 8:864 (2002); Lynch et al., Circ. Res., 80:197 (1997)).

Herpesvirus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes, e.g., genes encoding ryanodine receptors and titin.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, Nature, 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Synthetic Oligonucleotides

Antisense oligonucleotides are short (approximately 10 to 30 nucleotides in length), chemically synthesized DNA molecules that are designed to be complementary to the coding sequence of an RNA of interest. These agents may enter cells by diffusion or liposome-mediated transfer and possess relatively high transduction efficiency. These agents are useful to reduce or ablate the expression of a targeted gene while unmodified oligonucleotides have a short half-life in vivo, modified bases, sugars or phosphate groups can increase the half-life of oligonucleotide. For unmodified nucleotides, the efficacy of using such sequences is increased by linking the antisense segment with a specific promoter of interest, e.g., in an adenoviral construct. In one embodiment, electroporation and/or liposomes are employed to deliver plasmid vectors. Synthetic oligonucleotides may be delivered to cells as part of a macromolecular complex, e.g., a liposome, and delivery may be enhanced using techniques such as electroporation.

Regulatable Transcriptional Control Elements

The device of the invention may deliver one or more signals including, but not limited to, light of a particular wavelength or a range of wavelengths, light of a particular energy, acoustic energy, an electric field, a chemical, electromagnetic energy, thermal energy or other forms of temperature or matter, which signal is recognized by a regulatable transcriptional control element in a gene therapy vector.

A variety of strategies have been devised to control in vivo expression of transferred genes and thus alter the pharmacokinetics of in vivo gene transfer vectors in the context of regulatable or inducible promoters. Many of these regulatable promoters use exogenously administered agents to control transgene expression and some use the physiologic milieu to control gene expression. Examples of the exogenous control promoters include the tetracycline-responsive promoter, a chimeric transactivator consisting of the DNA and tetracycline-binding domains from the bacterial tet repressor fused to the transactivation domain of herpes simplex virion protein 16 (Ho et al., *Brain Res. Mol. Brain Res.,* 41:200 (1996)); a chimeric promoter with multiple cyclic adenosine monophosphate response elements superimposed on a minimal fragment of the 5'-flanking region of the cystic fibrosis transmembrane conductance regulator gene (Suzuki et al., 7:1883 (1996)); the EGR1 radiation-inducible promoter (Hallahan et al., *Nat. Med.,* 1:786 (1995)); and the chimeric GRE promoter (Lee et al., *J. Thoracic Cardio. Surg.,* 118:26 (1996)), with 5 GREs from the rat tyrosine aminotransferase gene in tandem with the insertion of Ad2 major late promoter TATA box-initiation site (Narumi et al., *Blood,* 92:812 (1998)). Examples of the physiologic control of promoters include a chimera of the thymidine kinase promoter and the thyroid hormone and retinoic acid-responsive element responsive to both exogenous and endogenous tri-iodothyronine (Hayashi et al., *J. Biol. Chem.,* 269:23872 (1994)); complement factor 3 and serum amyloid A3 promoters responsive to inflammatory stimuli; the grp78 and BiP stress-inducible promoter, a glucose-regulated protein that is inducible through glucose deprivation, chronic anoxia, and acidic pH (Gazit et al., *Cancer Res.,* 55:1660 (1995)); and hypoxia-inducible factor 1 and a heterodimeric basic helix-loop-helix protein that activates transcription of the human erythropoietin gene in hypoxic cells, which has been shown to act as a regulatable promoter in the context of gene therapy in vivo (Forsythe et al., *Mol. Cell Biol.,* 16:4604 (1996)).

Regulatable transcriptional elements useful in gene therapy vectors and methods of the invention include, but are not limited to, a truncated ligand binding domain of a progesterin receptor (controlled by antiprogestin), a tet promoter (controlled by tet and dox) (Dhawan et al., *Somat. Cell. Mol. Genet.,* 21, 233 (1995); Gossen et al., *Science,* 268:1766 (1995); Gossen et al., *Science,* 89:5547 (1992); Shockett et al., *Proc. Natl. Acad. Sci. USA,* 92, 6522 (1995)), hypoxia-inducible nuclear factors (Semenza et al., *Proc. Natl. Acad. Sci. USA,* 88, 5680 (1991); Semenza et al., *J. Biol. Chem.,* 269, 23757)), steroid-inducible elements and promoters, such as the glucocorticoid response element (GRE) (Mader and White, *Proc. Natl. Acad. Sci. USA,* 90, 5603 (1993)), and the fusion consensus element for RU486 induction (Wang et al., *Proc. Natl. Acad. Sci. USA,* 91:818 (1994)), those sensitive to electromagnetic fields, e.g., those present in metallothionein I or II, c-myc, and HSP70 promoters (Lin et al., *J. Cell. Biochem.,* 81:143 (2001); Lin et al., *J. Cell. Biochem.,* 54:281 (1994); U.S. published application 20020099026)), and electric pulses (Rubenstrunk et al., *J. Gene Med.,* 5:773 (2003)), as well as a yeast GAL4/TATA promoter, auxin inducible element, an ecdysone responsive element (No et al., *Proc. Natl. Acad. Sci. USA,* 93:3346 (1996)), an element inducible by rapamycin (FK506) or an analog thereof (Rivera et al., *Nat. Med.,* 2:1028 (1996); Ye et al., *Science,* 283:88 (1999); Rivera et al., *Proc. Natl. Acad. Sci. USA,* 96:8657 (1999)), a tat responsive element, a metal, e.g., zinc, inducible element, a radiation inducible element, e.g., ionizing radiation has been used as the inducer of the promoter of the early growth response gene (Erg-1) (Hallahan et al., *Nat. Med.,* 1:786 (1995)), an element which binds nuclear receptor PPARγ (peroxisome proliferators activated receptors), which is composed of a minimal promoter fused to PPRE (PPAR responsive elements, see WO 00/78986), a cytochrome P450/A1 promoter, a MDR-1 promoter, a promoter induced by specific cytokines (Varley et al., *Nat. Biotech.,* 15:1002 (1997)), a light inducible element (Shimizu-Sato et al., *Nat. Biotech.,* 20:1041 (2002)), a lacZ promoter, and a yeast Leu3 promoter.

In some embodiments, cell- or tissue-specific control elements, such as muscle-specific and inducible promoters, enhancers and the like, will be of particular use, e.g., in conjunction with regulatable transcriptional control elements. Such control elements include, but are not limited to, those derived from the actin and myosin gene families, such as from the myoD gene family (Weintraub et al., *Science,* 251, 761 (1991)); the myocyte-specific enhancer binding factor MEF-2 (Cserjesi and Olson, *Mol. Cell Biol.,* 11, 4854 (1991)); control elements derived from the human skeletal actin gene (Muscat et al., *Mol. Cell Bio.,* 7, 4089 (1987)) and the cardiac actin gene; muscle creatine kinase sequence elements (Johnson et al., *Mol. Cell Biol.,* 9, 3393 (1989)) and the murine creatine kinase enhancer (mCK) element; control elements derived from the skeletal fast-twitch troponin C gene, the slow-twitch cardiac troponin C gene and the slow-twitch troponin I genes.

Cardiac cell restricted promoters include but are not limited to promoters from the following genes: a α-myosin heavy chain gene, e.g., a ventricular α-myosin heavy chain gene, β-myosin heavy chain gene, e.g., a ventricular β-myosin heavy chain gene, myosin light chain 2v gene, e.g., a ventricular myosin light chain 2 gene, myosin light chain 2a gene, e.g., a ventricular myosin light chain 2 gene, cardiomyocyte-restricted cardiac ankyrin repeat protein (CARP) gene, cardiac α-actin gene, cardiac m2 muscarinic acetylcholine gene, ANP gene, BNP gene, cardiac troponin C gene, cardiac troponin I gene, cardiac troponin T gene, cardiac sarcoplasmic reticulum Ca-ATPase gene, skeletal α-actin gene, as well as an artificial cardiac cell-specific promoter.

Further, chamber-specific promoters or enhancers may also be employed, e.g., for atrial-specific expression, the quail slow myosin chain type 3 (MyHC3) or ANP promoter, or the cGATA-6 enhancer, may be employed. For ventricle-specific expression, the iroquois homeobox gene may be employed. Examples of ventricular myocyte-specific promoters include a ventricular myosin light chain 2 promoter and a ventricular myosin heavy chain promoter.

Nevertheless, other promoters and/or enhancers which are not specific for cardiac cells or muscle cells, e.g., RSV promoter, may be employed in the expression cassettes and methods of the invention. Other sources for promoters and/or enhancers are promoters and enhancers from the Csx/NKX 2.5 gene, titin gene, α-actinin gene, α-myosin heavy chain gene, myomesin gene, M protein gene, cardiac troponin T gene, RyR2 gene, Cx40 gene, and Cx43 gene, as well as genes which bind Mef2, dHAND, GATA, e.g., GATA-4 or GATA-6, CarG, E-box, Csx/NKX 2.5, or TGF-beta, or a combination thereof.

The response of the regulatable transcriptional control element to one or more intermittent signals, a prolonged signal or different levels of a signal, may be tested in vitro or in vivo. The vector may include the regulatable transcriptional control element linked to a marker gene, i.e., one which is readily detectable or capable of detection such as green fluorescent protein (GFP). For example, a vector having a promoter which is sensitive to electrical pulses, a MT-I or MT-II promoter (Rubenstruck et al., *J. Gene Med.*, 5:773 (2003)), is linked to an open reading frame for a marker gene. The resulting expression cassette, e.g., one which is introduced to an adenovirus vector or to a plasmid vector, is employed to infect or transfect murine cells, e.g., murine cardiac cells, or heart sections. An electrode system designed for use in a small flask is used to deliver electrical pulses. Then fluorescence in the cells or a lysate thereof is detected, and/or or vector specific RNA is measured, for instance, using RT-PCR, and optionally compared to data from control cells. Similarly, a vector having a promoter which is sensitive to electrical pulses is linked to an open reading frame for a therapeutic gene, e.g., Serca2, introduced to cells, e.g., cardiac cells such as those with decreased levels of the gene product encoded by the therapeutic gene, and the phenotype of the recombinant cells compared to control cells. Vectors may also be introduced to a non-human large animal model, e.g., pigs, to determine the level and spatial expression of the exogenously introduced gene in response to signals, e.g., electrical pulses, from an implantable device in that animal.

Exemplary Genes for Gene Therapy Vectors

Open reading frames useful in gene therapy vectors for cardiac protection biologic therapies include but are not limited to open reading frames for angiotensin, angiogenin 2, platelet-derived endothelial-cell growth factor (PD-ECGF), transforming growth factor-α (TGF-alpha), transforming growth factor-β (TGF-β), tumor necrosis factor-α (TNF-α), hepatocyte growth factor (HGF), vascular endothelial growth factor (VEGF), e.g., $VEGF_{145}$, $VEGF_{120}$, $VEGF_{121}$, $VEGF_{164}$, $VEGF_{165}$, $VEGF_{189}$, $VEGF_{206}$, VEGF-B, VEGF-C, VEGF-D, VEGF-E, or VEGF-F, fibroblast growth factor (FGF), such as acidic-FGF, basic-FGF, FGF-1, FGF-2, FGF-3, FGF-4, FGF-5, FGF-6, FGF-7, FGF-8 or FGF-9, angiopoietin-1, or hypoxia inducible factor 1α (HIF-1α). In particular, gene products associated with cardiac protection include, but are not limited to, those encoded by antioxidant genes, e.g., HO-1, SOD, catalase, or GPx, heat shock proteins, e.g., HSP70, HSP90, or HSP27, gene products that enhance survival, e.g., Bcl-2, Akt, and HGF, inflammatory cytokines, adhesion molecules, or transcription factors, e.g., ICAM, VCAM, TNF-α, and $NF_{-k}B$, gene products associated with apoptosis, e.g., Bad, caspase inhibitors, p53, p38-MAPK, or Fas ligand, gene products that enhance coronary vessel tone, e.g., eNOS or adenosine (P1, P3) receptors, and gene products associated with cardiac rescue, e.g., proangiogenic factors, including $VEGF_{121}$, $VEGF_{165}$, FGF-1, FGF-2, FGF-4, FGF-5, HGF, eNOS, Ang-1, MCP-1, G-CSF, PDGF-BB, IGF-1, IGF-2, HIF-1α/VP16, egr-1, and Prox-1, as well as pleiotrophin, phosphodiesterase (PDE) inhibitors, e.g., inhibitors of PDE5, platelet derived endothelial cell growth factor (PD-ECGF), and tissue inhibitor of metalloproteinase.

Vector Delivery

Several techniques have been developed for cardiac gene delivery, including pericardial infusion, endomyocardial injection, intracoronary injection, coronary venous retroperfusion, and aortic root injection (Isner, *Nature,* 415:234 (2002)). The different techniques achieve variable response in homogeneity of gene delivery, resulting in focal gene expression within the heart (Hajjar et al., *Circ. Res.,* 86:616 (2000)). For this reason, techniques that achieve diffuse uptake would seem to be superior. Two such methods utilize the heart's arterial and venous circulation to accomplish disseminated viral transfection. Arterial injection, performed directly through a percutaneous approach or indirectly by an infusion into the cross-clamped aorta, has shown promise in animal models of heart failure and is appealing in that it can be performed either at the time of cardiac surgery or as percutaneous intervention (Hajjar et al., *PNAS USA,* 95:5251 (1998)). Similarly, retroperfusion through the coronary sinus appears to produce a more global gene expression in comparison with techniques of localized or focal injection (Boeckstegers et al., *Circ.,* 100:1 (1999)).

Vectors may be administered intravenously, transvenously, intramyocardially or by any other convenient route, and delivered by a needle, catheter, e.g., a catheter which includes an injection needle or infusion port, or other suitable device.

Direct Myocardial Injection

Direct myocardial injection of plasmid DNA as well as virus vectors, e.g., adenoviral vectors, and cells including recombinant cells has been documented in a number of in vivo studies. This technique when employed with plasmid DNA or adenoviral vectors has been shown to result in effective transduction of cardiac myocytes. Thus, direct injection may be employed as an adjunct therapy in patients undergoing open-heart surgery or as a stand-alone procedure via a modified thorascope through a small incision. In one embodiment, this mode of administration is used to deliver a gene or gene product that would only require limited transfection efficiency to produce a significant therapeutic response, such as a gene that encodes for or leads to a secreted product (e.g., VEGF, endothelial nitric oxide synthase). Virus, e.g., pseudotyped, or DNA- or virus-liposome complexes may be delivered intramyocardially.

Catheter-based Delivery

Intracoronary delivery of genetic material can result in transduction of approximately 30% of the myocytes predominantly in the distribution of the coronary artery. Parameters influencing the delivery of vectors via intracoronary perfusion and enhancing the proportion of myocardium transduced include a high coronary flow rate, longer exposure time, vector concentration, and temperature. Gene delivery to a substantially greater percent of the myocardium may be enhanced by administering the gene in a low-calcium, high-serotonin mixture (Donahue et al., *Nat. Med.,* 6:1395 (2000)). The potential use of this approach for gene therapy for heart failure may be increased by the use of specific proteins that enhance myocardial uptake of vectors (e.g., cardiac troponin T).

Improved methods of catheter-based gene delivery have been able to achieve almost complete transfection of the myocardium in vivo. Hajjar et al. (*Proc. Natl. Acad. Sci. USA,* 95:5251 (1998)) used a technique combining surgical catheter insertion through the left ventricular apex and across the aortic valve with perfusion of the gene of interest during cross-clamping of the aorta and pulmonary artery. This technique resulted in almost complete transduction of the heart and could serve as a protocol for the delivery of adjunctive gene therapy during open-heart surgery when the aorta can be cross-clamped.

Pericardial Delivery

Gene delivery to the ventricular myocardium by injection of genetic material into the pericardium has shown efficient gene delivery to the epicardial layers of the myocardium. However, hyaluronidase and collagenase may enhance transduction without any detrimental effects on ventricular function.

Intravenous Delivery

Intravenous gene delivery may be efficacious for myocardial gene delivery. However, to improve targeted delivery and transduction efficiency of intravenously administered vectors, targeted vectors may be employed. In one embodiment, intravenous administration of DNA-liposome or antibody-DNA complexes may be employed.

Lead-based Delivery

Gene delivery can be performed by incorporating a gene delivery device or lumen into a lead such as a pacing lead, defibrillation lead, or pacing-defibrillation lead. An endocardial lead including a gene delivery device or lumen allows gene delivery to the endocardial layers of the myocardium. An epicardial lead including a gene delivery device or lumen allows gene delivery to the endocardial layers of the myocardium. A transvenous lead including a gene delivery device or lumen may also allow intravenous gene delivery. Lead-based delivery is particularly advantageous when the lead is used to deliver electrical and gene therapies to the same region.

Generally any route of administration may be employed, including oral, mucosal, intramuscular, buccal and rectal administration. For certain vectors, certain route of administration may be preferred. For instance, viruses, e.g., pseudotyped virus, and DNA- or virus-liposome, e.g., HVJ-liposome, may be administered by coronary infusion, while HVJ-liposome complexes may be delivered pericardially.

Dosages and Dosage Forms

The amount of gene therapy vector(s), e.g., those which are present in a recombinant cell or in acellular form, including acellular complexes, administered and device based signal emitted to achieve a particular outcome will vary depending on various factors including, but not limited to, the gene and promoter chosen, the condition, patient specific parameters, e.g., height, weight and age, and whether prevention or treatment is to be achieved. The gene regulatory system of the invention is amenable to chronic use for prophylactic purposes.

Vectors of the invention may conveniently be provided in the form of formulations suitable for administration, e.g., into the blood stream (e.g., in an intracoronary artery). A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about $10^7$ viral particles, preferably about $10^9$ viral particles, and more preferably about $10^{11}$ viral particles. The number of viral particles may, but preferably does not exceed $10^{14}$. As noted, the exact dose to be administered is determined by the attending clinician, but is preferably in 1 ml phosphate buffered saline. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

In one embodiment, administration may be by intracoronary injection to one or both coronary arteries (or to one or more saphenous vein or internal mammary artery grafts or other conduits) using an appropriate coronary catheter. A variety of catheters and delivery routes can be used to achieve intracoronary delivery, as is known in the art. For example, a variety of general purpose catheters, as well as modified catheters, suitable for use in the present invention are available from commercial suppliers. Also, where delivery to the myocardium is achieved by injection directly into a coronary artery, a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., above, including: Topol, (ed.), *The Textbook of Interventional Cardiology*, 4th Ed. (Elsevier 2002); Rutherford, *Vascular Surgery*, 5th Ed. (W.B. Saunders Co. 2000); Wyngaarden et al. (eds.), *The Cecil Textbook of Medicine*, 22nd Ed. (W.B. Saunders, 2001); and Sabiston, *The Textbook of Surgery*, 16th Ed. (Elsevier 2000)).

By way of illustration, liposomes and other lipid-containing gene delivery complexes can be used to deliver one or more transgenes. The principles of the preparation and use of such complexes for gene delivery have been described in the art (see, e.g., Ledley, *Human Gene Therapy*, 6:1129 (1995); Miller et al., *FASEB Journal*, 9:190 (1995); Chonn et al., *Curr. Opin. Biotech.*, 6:698 (1995); Schofield et al., *British Med. Bull.*, 51:56 (1995); Brigham et al., *J. Liposome Res.*, 3:31 (1993)).

Administration of the gene therapy vector in accordance with the present invention may be continuous or intermittent, depending, for example, upon the recipient's physiological condition, whether the purpose of the administration is therapeutic or prophylactic, and other factors known to skilled practitioners. The administration of the gene therapy vector may be essentially continuous over a preselected period of time or may be in a series of spaced doses. Both local and systemic administration is contemplated.

One or more suitable unit dosage forms comprising the gene therapy vector, which may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

Pharmaceutical formulations containing the gene therapy vector can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions for convenient oral administration or as solutions appropriate for parenteral administration, for instance by intramuscular, subcutaneous or intravenous routes.

The pharmaceutical formulations of the vectors can also take the form of an aqueous or anhydrous solution or dispersion, or alternatively the form of an emulsion or suspension.

Thus, the vector may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

The local delivery of the vectors can also be by a variety of techniques which administer the vector at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

When desired, the above-described formulations can be adapted to give sustained release of the active ingredient employed, e.g., by combination with certain hydrophilic polymer matrices, e.g., comprising natural gels, synthetic polymer gels or mixtures thereof.

The formulations and compositions described herein may also contain other ingredients such as antimicrobial agents or preservatives.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for cardiac protection, the method comprising:
   sensing one or more parameters indicative of an ischemic event in a mammal using an implantable medical device;
   detecting the ischemic event from the one or more parameters, including detecting an end of the ischemic event, using the implantable medical device;
   initiating one or more cardiac protection biologic therapies using the implantable medical device in response to the detection of the ischemic event, the one or more cardiac protection biologic therapies each including at least one signaling and non-signaling period, the at least one signaling period having a signaling duration during which at least one gene regulatory signal is delivered, the at least one non-signaling period having a non-signaling duration during which the at least one gene regulatory signal is not delivered, the at least one gene regulatory signal is capable of directly or indirectly regulating a regulatable transcriptional control element without inducing cardiac depolarization, the regulatable transcriptional control element is operably linked to an open reading frame forming an expression cassette, wherein the expression cassette is present in the mammal, and wherein expression of the open reading frame in an effective amount inhibits damage to tissue in the mammal resulting from ischemia; and
   delivering the at least one gene regulatory signal from the implantable medical device during at least one of the signaling periods,
   wherein the one or more cardiac protection biologic therapies include at least one postconditioning cardiac biologic therapy, and initiating the one or more cardiac protection biologic therapies includes initiating the at least one postconditioning cardiac biologic therapy using the implantable medical device when a post-ischemia time interval expires, the post-ischemia time interval starting at the detected end of the ischemic event and ending after a predicted reperfusion period following the ischemic event has started.

2. The method of claim 1, wherein the post-ischemia time interval is up to approximately 10 minutes.

3. The method of claim 1, further comprising timing the at least one postconditioning cardiac biologic therapy including alternating postconditioning signaling and non-signaling periods, the at least one postconditioning cardiac biologic therapy having a postconditioning therapy duration in a range of approximately 30 seconds to 1 hour, the postconditioning signaling period having a postconditioning signal duration in a range of approximately 5 seconds to 10 minutes during which the at least one gene regulatory signal is delivered, the postconditioning non-signaling period having a postconditioning non-signal duration in a range of approximately 5 seconds to 10 minutes during which the at least one gene regulatory signal is not delivered.

4. The method of claim 1, wherein the one or more cardiac protection biologic therapies further comprise a plurality of preconditioning cardiac biologic therapies, and further comprising initiating the preconditioning cardiac biologic therapies after the postconditioning cardiac biologic therapy is completed.

5. The method of claim 4, wherein initiating the preconditioning cardiac biologic therapies comprises initiating the preconditioning cardiac biologic therapies on a periodic basis using a predetermined period in a range of approximately 24 hours to 72 hours.

6. The method of claim 4, wherein initiating the preconditioning cardiac biologic therapies comprises initiating the preconditioning cardiac biologic therapies in response to one or more preconditioning commands.

7. The method of claim 4, further comprising timing the plurality of preconditioning cardiac biologic therapies each including alternating preconditioning signaling and non-signaling periods, the preconditioning cardiac biologic therapies each having a preconditioning therapy duration in a range of approximately 2 minutes to 1 hour, the preconditioning signaling period each having a preconditioning signal duration in a range of approximately 1 minute to 30 minutes during which the at least one gene regulatory signal is delivered, the preconditioning non-signaling period having a preconditioning non-signal duration in a range of approximately 1 minute to 30 minutes during which the at least one gene regulatory signal is not delivered.

8. The method of claim 1, further comprising:
detecting an arrhythmia; and
suspending the one or more cardiac protection biologic therapies when the arrhythmia is detected.

9. The method of claim 1, wherein delivering the at least one gene regulatory signal comprises generating an electric field having frequency and strength parameters selected for regulating the regulatable transcriptional control element.

10. The method of claim 1, wherein delivering the at least one gene regulatory signal comprises generating an electromagnetic field having frequency and strength parameters selected for regulating the regulatable transcriptional control element.

11. The method of claim 1, wherein delivering the at least one gene regulatory signal comprises emitting a light having wavelength and intensity parameters selected for regulating the regulatable transcriptional control element.

12. The method of claim 1, wherein delivering the at least one gene regulatory signal comprises emitting an acoustic signal having frequency and intensity parameters selected for regulating the regulatable transcriptional control element.

13. The method of claim 1, wherein delivering the at least one gene regulatory signal comprises emitting one or more chemical agents regulating the regulatable transcriptional control element.

14. The method of claim 1, wherein delivering the at least one gene regulatory signal comprises emitting a thermal energy for regulating the regulatable transcriptional control element.

15. The method of claim 1, wherein initiating the one or more cardiac protection biologic therapies in response to the detection of the ischemic event comprises initiating a postconditioning cardiac biologic therapy of the one or more cardiac protection biologic therapies in response to expiration of a post-ischemia time interval that starts at the end of the ischemic event and ends after a predicted reperfusion period following the ischemic event has started.

16. A method for cardiac protection, the method comprising:
receiving a command;
sensing one or more parameters indicative of an ischemic event using an implantable medical device;
detecting the ischemic event from the one or more parameters, including detecting an end of the ischemic event, using the implantable medical device;
initiating one or more cardiac protection biologic therapies in response to one or more of the reception of the command and the detection of the ischemic event, the one or more cardiac protection biologic therapies each including at least one signaling and non-signaling period, the at least one signaling period having a signaling duration during which at least one gene regulatory signal is delivered, the at least one non-signaling period having a non-signaling duration during which the at least one gene regulatory signal is not delivered, the at least one gene regulatory signal is capable of directly or indirectly regulating a regulatable transcriptional control element without inducing cardiac depolarization, the regulatable transcriptional control element is operably linked to an open reading frame forming an expression cassette, wherein the expression cassette is present in the mammal, and wherein expression of the open reading frame in an effective amount inhibits damage to cardiac tissue resulting from ischemia; and
delivering the at least one gene regulatory signal from the implantable medical device during at least one of the signaling periods,
wherein initiating the one or more cardiac protection biologic therapies comprises initiating at least one postconditioning cardiac biologic therapy using the implantable medical device in response to one or more of the reception of the command and when a post-ischemia time interval expires, the post-ischemia time interval starting at the detected end of the ischemic event and ending after a predicted reperfusion period following the ischemic event has started.

17. The method of claim 16, wherein receiving the command comprises receiving the command using a user input device of an external system communicatively coupled to the implantable medical device.

18. The method of claim 17, wherein delivering the at least one gene regulatory signal comprises generating an electric or electromagnetic field having frequency and strength parameters selected for regulating the regulatable transcriptional control element.

19. The method of claim 16, wherein the post-ischemia time interval is up to approximately 10 minutes.

20. The method of claim 16, comprising timing the signaling and non-signaling durations each being a duration between approximately 5 seconds and 30 minutes.

* * * * *